(12) United States Patent
Jordan et al.

(10) Patent No.: US 7,155,373 B2
(45) Date of Patent: Dec. 26, 2006

(54) SELECTION OF ORTHODONTIC BRACKETS

(75) Inventors: Russell A. Jordan, Rancho Cucamonga, CA (US); Ming-Lai Lai, Arcadia, CA (US); James D. Cleary, Glendora, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 765 days.

(21) Appl. No.: 10/081,220

(22) Filed: Feb. 22, 2002

(65) Prior Publication Data

US 2003/0163291 A1 Aug. 28, 2003

(51) Int. Cl.
G06F 17/50 (2006.01)

(52) U.S. Cl. ............................................ 703/1; 433/24

(58) Field of Classification Search .................... 703/1; 433/24, 3
See application file for complete search history.

(56) References Cited

U.S. PATENT DOCUMENTS

| | | | |
|---|---|---|---|
| 3,861,044 A | 1/1975 | Swinson, Jr. | |
| 4,204,325 A | 5/1980 | Kaelble | |
| 4,528,627 A | 7/1985 | Coben | |
| 4,611,288 A | 9/1986 | Duret et al. | |
| 4,668,192 A | 5/1987 | Lavin | |
| 4,742,464 A | 5/1988 | Duret et al. | |
| 4,837,732 A | 6/1989 | Brandestini et al. | |
| 4,919,615 A | 4/1990 | Croll | |
| 4,964,770 A | 10/1990 | Steinbichler et al. | |
| 5,011,405 A * | 4/1991 | Lemchen ..................... | 433/24 |
| 5,027,281 A | 6/1991 | Rekow et al. | |
| 5,078,599 A | 1/1992 | Eenboom et al. | |
| 5,131,844 A | 7/1992 | Marinaccio et al. | |
| 5,139,419 A | 8/1992 | Andreiko et al. | |
| 5,212,871 A | 5/1993 | Luccarelli | |
| 5,237,998 A | 8/1993 | Duret et al. | |
| 5,266,030 A | 11/1993 | Van Der Zel | |
| 5,278,756 A | 1/1994 | Lemchen et al. | |
| 5,322,436 A | 6/1994 | Horng et al. | |
| 5,338,198 A | 8/1994 | Wu et al. | |
| 5,342,194 A | 8/1994 | Feldman | |
| 5,354,199 A | 10/1994 | Jacobs et al. | |
| 5,368,478 A | 11/1994 | Andreiko et al. | |
| 5,372,502 A | 12/1994 | Massen et al. | |
| 5,395,238 A | 3/1995 | Andreiko et al. | |
| 5,417,572 A | 5/1995 | Kawai et al. | |
| 5,454,717 A | 10/1995 | Andreiko et al. | |

(Continued)

FOREIGN PATENT DOCUMENTS

CA 2292141 6/2001

(Continued)

OTHER PUBLICATIONS

Mortenson, Michael E.; "Geometric Modeling", 1985, John Wiley & Sons.*

(Continued)

Primary Examiner—Paul Rodriguez
Assistant Examiner—Russ Guill
(74) Attorney, Agent, or Firm—James D. Christoff

(57) ABSTRACT

Selection of orthodontic brackets from predefined and existing orthodontic brackets is provided by a user viewing a patient's teeth and using, for example, a user interface, to define a three-dimensional tooth/arch model from three-dimensional model data. Likewise, a prescription is selected. With such information, the teeth of the defined tooth/arch model can be positioned in prescribed positions. Once modifications to the prescription or for that matter the patient's tooth/arch model, if any, are made, predefined and existing orthodontic brackets can be selected, e.g., such selection can be based on selection criteria used to search a database including parameters defining such predefined and existing orthodontic brackets.

58 Claims, 16 Drawing Sheets

U.S. PATENT DOCUMENTS

| | | | |
|---|---|---|---|
| RE35,169 E | 3/1996 | Lemchen et al. | |
| 5,518,397 A | 5/1996 | Andreiko et al. | |
| 5,533,895 A | 7/1996 | Andreiko et al. | |
| 5,538,129 A | 7/1996 | Chester et al. | |
| 5,575,645 A | 11/1996 | Jacobs et al. | |
| 5,605,459 A | 2/1997 | Kuroda et al. | |
| 5,674,069 A | 10/1997 | Osorio | |
| 5,683,243 A | 11/1997 | Andreiko et al. | |
| 5,851,115 A | 12/1998 | Carlsson et al. | |
| 5,879,158 A | 3/1999 | Doyle et al. | |
| 5,882,192 A | 3/1999 | Bergersen | |
| 5,975,893 A | 11/1999 | Chishti et al. | |
| 6,068,482 A | 5/2000 | Snow | |
| 6,089,868 A | 7/2000 | Jordan et al. | |
| 6,152,731 A | 11/2000 | Jordan et al. | |
| 6,227,850 B1 | 5/2001 | Chishti et al. | |
| 6,244,861 B1 | 6/2001 | Andreiko et al. | |
| 6,250,918 B1 | 6/2001 | Sachdeva et al. | |
| 6,309,215 B1 | 10/2001 | Phan et al. | |
| 6,315,553 B1 | 11/2001 | Sachdeva et al. | |
| 6,318,994 B1 | 11/2001 | Chishti et al. | |
| 6,350,119 B1 | 2/2002 | Jordan et al. | |
| 6,350,120 B1 | 2/2002 | Sachdeva et al. | |
| 6,632,089 B1 * | 10/2003 | Rubbert et al. | 433/24 |
| 6,736,638 B1 * | 5/2004 | Sachdeva et al. | 433/24 |
| 6,739,869 B1 * | 5/2004 | Taub et al. | 433/24 |
| 2001/0002310 A1 | 5/2001 | Chishti et al. | |
| 2002/0015934 A1 | 2/2002 | Rubbert et al. | |

FOREIGN PATENT DOCUMENTS

| | | |
|---|---|---|
| DE | 38 10 455 | 10/1989 |
| DE | 196 51 223 | 6/1998 |
| EP | 0 502 227 | 9/1992 |
| EP | 0 634 150 | 1/1995 |
| EP | 0696444 | 2/1996 |
| EP | 0595231 | 4/1997 |
| IL | 114691 | 7/1995 |
| IL | 118523 | 5/1996 |
| IL | 120867 | 5/1997 |
| IL | 120892 | 5/1997 |
| IL | 121872 | 9/1997 |
| WO | WO 90/08512 | 8/1990 |
| WO | WO 96/28112 | 9/1996 |
| WO | WO 97/03622 | 2/1997 |
| WO | WO 99/16380 | 4/1999 |
| WO | WO 99/34747 | 7/1999 |
| WO | WO 00/19931 | 4/2000 |
| WO | WO 01/80765 | 11/2001 |
| WO | WO 01/82192 | 11/2001 |
| WO | WO 01/85047 | 11/2001 |
| WO | WO 01/87179 | 11/2001 |

OTHER PUBLICATIONS

The Orthos Approach . . . The First Comprehensive Appliance System Designed to Address Common Clinical Problems, Product literature of Ormco Company, 7 pages, undated.

"Biomechanics in Orthodontics," Product literature of Giorgio Fiorelli—Birte Melsen, 2 pages, undated.

T. Kuroda et al., "Three-dimensional dental cast analyzing system using laser scanning", J. Am. Ortho. Dent. Orthop., 110, 365-369 (Oct. 1996).

D. Laurendeau et al., "A Computer-Vision Technique for the Acquisition and Processing of 3-D Profiles of Dental Imprints: An Application I Orthodontics", IEEE Transactions on Medical Imaging, 10, 453-461 (Sep. 1991).

Pending U.S. Appl. No. 09/918,226, filed Jul. 30, 2001.

* cited by examiner

| | Tooth # | 7 | 6 | 5 | 4 | 3 | 2 | 1 |
|---|---|---|---|---|---|---|---|---|
| Upper Arch | in/out, mm | 1 | 1 | 1.4 | 1.5 | 1.4 | 2.25 | 1.8 |
| | Angulation, deg | 5 | 5 | 2 | 2 | 11 | 9 | 5 |
| | Torque, deg | -9 | -9 | -7 | -7 | -7 | 3 | 7 |
| Lower Arch | in/out, mm | 1 | 1 | 1.15 | 1.15 | 1.6 | 2.3 | 2.3 |
| | Angulation, deg | 2 | 2 | 2 | 2 | 5 | 2 | 2 |
| | Torque, deg | -35 | -30 | -22 | -17 | -11 | -1 | -1 |

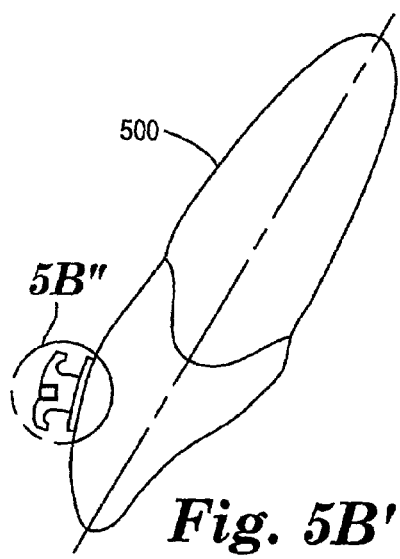
Fig. 5B'
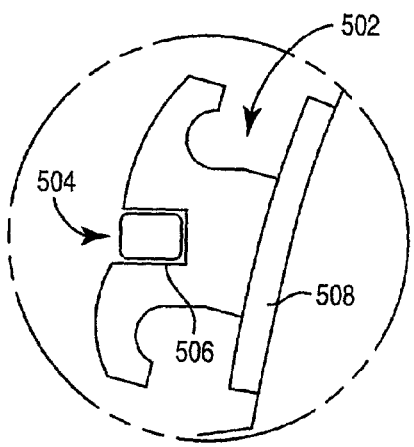
Fig. 5B"
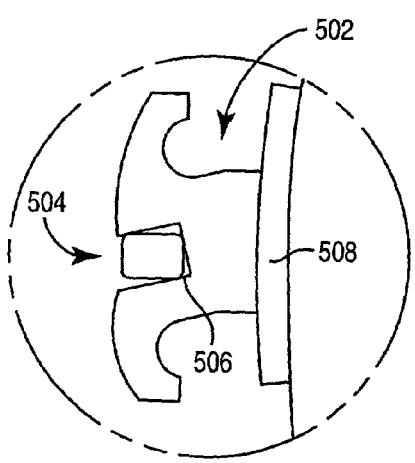
Fig. 5C"
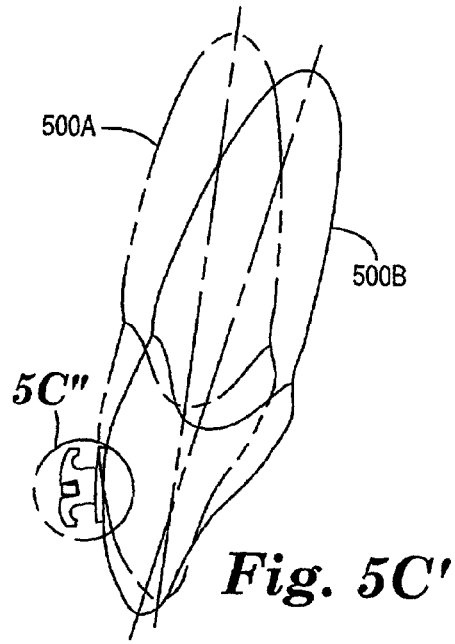
Fig. 5C'
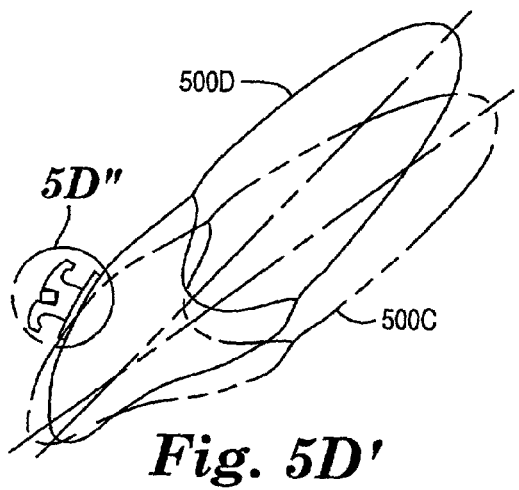
Fig. 5D'
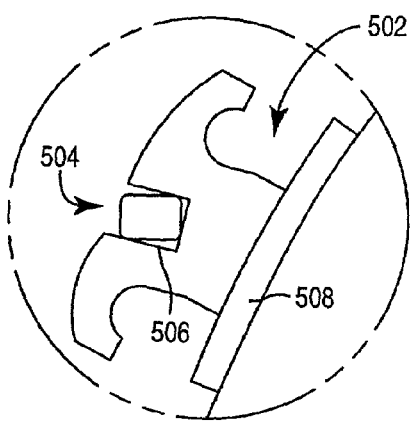
Fig. 5D"

Bracket Selection Criteria

402

| Lower arch bracket name | torque, deg. | angulation, deg. | angulation, deg. | in/out, mm | left/right |
|---|---|---|---|---|---|
| Anterior | >-5 | 0 | 0 | 1.5 | L/R |
| Cuspid | -7 | >=2 | <=5 | 0.76 | L |
| 1st Bicuspid | -7 | 0 | 0 | 0.76 | L/R |
| 2nd Bicuspid | -17 | >=2 | <=4 | 0.89 | L |

*Fig. 12A*

Brackets Selected Using Advanced Filtering with Selection Criteria Above

| Lower arch bracket name | torque, deg. | angulation, deg. | in/out, mm | hook | left/right | part no. for .018" slot | part no. for .022" slot |
|---|---|---|---|---|---|---|---|
| Anterior | -1 | 0 | 1.5 | | L/R | 017-419 | 017-519 |
| Anterior | -1 | 0 | 1.5 | D | L/R | 017-440 | 017-540 |
| Anterior | 0 | 0 | 1.5 | | L/R | 017-603 | 017-703 |
| Cuspid | -7 | 5 | 0.76 | | L | 017-579 | 017-679 |
| Cuspid | -7 | 5 | 0.76 | M | L | 017-611 | 017-711 |
| Cuspid | -7 | 5 | 0.76 | D | L | 017-581 | 017-681 |
| 1st Bicuspid | -7 | 0 | 0.76 | | L/R | 017-805 | 017-905 |
| 2nd Bicuspid | -17 | 2 | 0.89 | | L | 017-797 | 017-897 |
| 2nd Bicuspid | -17 | 2 | 0.89 | D | L | 017-811 | 017-911 |

Brackets in Database

| Lower arch bracket name | torque, deg. | angulation, deg. | in/out, mm | hook | left/right | part no. for .018" slot | part no. for .022" slot |
|---|---|---|---|---|---|---|---|
| Anterior | -1 | 0 | 1.5 | | L/R | 017-419 | 017-519 |
| Anterior | -1 | 0 | 1.5 | D | LL | 017-439 | 017-539 |
| Anterior | -1 | 0 | 1.5 | D | L/R | 017-440 | 017-540 |
| Anterior | -1 | 0 | 1.2 | | L/R | 017-660 | 017-760 |
| Anterior | -6 | 0 | 1.5 | | L/R | 017-792 | 017-892 |
| Anterior | -5 | 0 | 1 | | L/R | 017-422 | 017-522 |
| Anterior | -5 | 0 | 1.5 | D | LL | 017-441 | 017-541 |
| Anterior | -5 | 0 | 1.5 | D | L/R | 017-442 | 017-542 |
| Anterior | -10 | 0 | 1.5 | | L/R | 017-613 | 017-713 |
| Anterior | 0 | 0 | 1.5 | | L/R | 017-603 | 017-703 |
| Cuspid | -7 | 6 | 0.76 | | L | 017-427 | 017-527 |
| Cuspid | -7 | 6 | 0.76 | | R | 017-428 | 017-528 |
| Cuspid | -7 | 6 | 0.76 | D | L | 017-429 | 017-529 |
| Cuspid | -7 | 6 | 0.76 | D | R | 017-430 | 017-530 |
| Cuspid | -6 | 3 | 0.76 | | L | 017-793 | 017-893 |
| Cuspid | -6 | 3 | 0.76 | | R | 017-794 | 017-894 |
| Cuspid | -7 | 5 | 0.76 | | L | 017-579 | 017-679 |
| Cuspid | -7 | 5 | 0.76 | | R | 017-580 | 017-680 |
| Cuspid | -7 | 5 | 0.76 | M | L | 017-611 | 017-711 |
| Cuspid | -7 | 5 | 0.76 | M | R | 017-612 | 017-712 |
| Cuspid | -7 | 5 | 0.76 | D | L | 017-581 | 017-681 |
| Cuspid | -7 | 5 | 0.76 | D | R | 017-582 | 017-682 |
| Cuspid | 0 | 3 | 0.76 | D | L | 017-771 | 017-871 |
| Cuspid | 0 | 3 | 0.76 | D | R | 017-772 | 017-872 |
| Cuspid | 0 | 0 | 0.79 | | L | 017-643 | 017-743 |
| Cuspid | 0 | 0 | 0.79 | | R | 017-644 | 017-744 |
| Cuspid | 0 | 0 | 0.79 | D | L | 017-645 | 017-745 |
| Cuspid | 0 | 0 | 0.79 | D | R | 017-646 | 017-746 |
| 1st Bicuspid | -7 | 0 | 0.76 | | L/R | 017-805 | 017-905 |
| 1st Bicuspid | -7 | 0 | 0.76 | D | L | 017-807 | 017-907 |
| 1st Bicuspid | -7 | 0 | 0.76 | D | R | 017-806 | 017-906 |
| 1st Bicuspid | -11 | 0 | 0.89 | | L/R | 017-586 | 017-686 |
| 1st Bicuspid | -11 | 0 | 0.89 | D | L | 017-587 | 017-687 |
| 1st Bicuspid | -11 | 0 | 0.89 | D | R | 017-588 | 017-688 |
| 1st Bicuspid | -11 | 0 | 0.89 | M | L | 017-649 | 017-749 |
| 1st Bicuspid | -11 | 0 | 0.89 | M | R | 017-650 | 017-650 |
| 1st Bicuspid | -12 | 2 | 0.89 | | L | 017-795 | 017-895 |
| 1st Bicuspid | -12 | 2 | 0.89 | | R | 017-796 | 017-896 |
| 1st Bicuspid | -12 | 2 | 0.89 | D | L | 017-809 | 017-909 |
| 1st Bicuspid | -12 | 2 | 0.89 | D | R | 017-808 | 017-908 |
| 1st Bicuspid | -17 | 0 | 0.89 | | L/R | 017-616 | 017-716 |
| 1st Bicuspid | -17 | 0 | 0.89 | D | L | 017-615 | 017-715 |
| 1st Bicuspid | -17 | 0 | 0.89 | D | R | 017-614 | 017-714 |
| 1st Bicuspid | -17 | 0 | 0.89 | M | L | 017-651 | 017-751 |
| 1st Bicuspid | -17 | 0 | 0.89 | M | R | 017-652 | 017-752 |
| 1st Bicuspid | 0 | 0 | 0.91 | | L/R | 017-599 | 017-699 |
| 1st Bicuspid | 0 | 0 | 0.91 | D | L | 017-601 | 017-701 |
| 1st Bicuspid | 0 | 0 | 0.91 | D | R | 017-602 | 017-702 |
| 2nd Bicuspid | -17 | 0 | 0.89 | | L/R | 017-589 | 017-689 |
| 2nd Bicuspid | -17 | 0 | 0.89 | D | L | 017-591 | 017-691 |
| 2nd Bicuspid | -17 | 0 | 0.89 | D | R | 017-590 | 017-690 |
| 2nd Bicuspid | -17 | 0 | 0.89 | M | L | 017-653 | 017-753 |
| 2nd Bicuspid | -17 | 0 | 0.89 | M | R | 017-654 | 017-754 |
| 2nd Bicuspid | -17 | 2 | 0.89 | | L | 017-797 | 017-897 |
| 2nd Bicuspid | -17 | 2 | 0.89 | | R | 017-798 | 017-898 |
| 2nd Bicuspid | -17 | 2 | 0.89 | D | L | 017-811 | 017-911 |
| 2nd Bicuspid | -17 | 2 | 0.89 | D | R | 017-810 | 017-910 |
| 2nd Bicuspid | -22 | 0 | 0.89 | | L/R | 017-592 | 017-692 |
| 2nd Bicuspid | -22 | 0 | 0.89 | D | L | 017-593 | 017-693 |
| 2nd Bicuspid | -22 | 0 | 0.89 | D | R | 017-594 | 017-694 |
| 2nd Bicuspid | -22 | 0 | 0.89 | M | L | 017-655 | 017-755 |
| 2nd Bicuspid | -22 | 0 | 0.89 | M | R | 017-656 | 017-756 |

D=Dolichofacial
M=Mesofacial

*Fig. 12B*

SELECTION OF ORTHODONTIC BRACKETS

FIELD OF THE INVENTION

The present invention relates to orthodontia. More particularly, the present invention relates to the selection of orthodontic appliances, e.g., orthodontic brackets.

DESCRIPTION OF THE RELATED ART

Orthodontia is a branch of dentistry that prevents or treats irregular positions of the teeth. Teeth that are not in correct positions may hinder proper chewing of food, and may also tend to develop caries or contribute to gum disease. Furthermore, malpositioned or maloccluded teeth may present an unsightly appearance, especially if located in the anterior portions of the patient's oral cavity.

An orthodontic brace is a device used to move teeth to orthodontically correct positions along the dental arch. Typically, the orthodontic practitioner will create a custom orthodontic brace for each patient by selecting components that apply gentle pressure to the teeth in certain directions. Over a period of time, the teeth tend to slowly shift toward desired positions. After an extended period of time, the growth of new bone tissue in areas next to the roots of the teeth hold the teeth in their new positions.

One type of orthodontic brace that is in widespread use includes a set of orthodontic appliances along with an archwire. The appliances typically include a number of small, slotted brackets, each of which is mounted on a corresponding tooth along the dental arch. An archwire is received in the slot of each bracket and forms a track to guide the teeth toward desired positions. Usually a set of appliances and an archwire are provided for both the upper and the lower dental arch of the patient. In other words, treatment of both arches is generally carried out at the same time.

There are numerous methods for selecting orthodontic appliances and archwires. Particular selection methods used by a practitioner are generally related to the type of orthodontic techniques that are expected to be employed during the course of orthodontic therapy. For example, one exemplary technique is known as the "straight wire" technique. This technique involves the use of brackets having slots that are designed to be in a common plane once the teeth have moved to desired, final positions. Although the slots of the brackets are not aligned at the beginning of treatment due to the various malpositions of the teeth, the inherent resilience of the archwire provides a restoring force that tends to move the archwire and hence the slots of the associated brackets into alignment in a common plane.

In the straight wire technique described above, each of the selected brackets has a certain "prescription" that represents particular characteristics of the bracket. The prescription can include numerous different aspects or features of the bracket, such as the size of the archwire slot, as well as orientation of a slot relative to a base of the bracket that is intended to be mounted on a surface of the tooth. The prescription describes the orientation of the archwire slot relative to the base of the bracket and may include values for torque, angulation, and rotation. In terms of tooth movement, "torque" is often defined as tipping movement of the long axis of the tooth in a buccolabial-lingual direction (i.e., in directions toward and away from the patient's lips or cheeks and the patient's tongue), "angulation" is defined as tipping movement of the long axis of the tooth in mesial and distal directions (i.e., in directions toward and away from the center of the patient's dental arch), and "rotation" is defined as rotational movement of the tooth about its long axis.

The prescription for orthodontic brackets often varies from tooth to tooth to achieve desired tooth positions. For example, many practitioners prefer that the long axes of the lower anterior teeth be as upright as possible, and consequently will prescribe for those teeth a bracket having torque and angulation values of zero (0). In contrast, the upper central incisor teeth normally have long axes that are slanted. As a result, the practitioner may prescribe upper central brackets having a torque of, for example, 17 degrees and an angulation of, for example, 5 degrees. However, the desired prescription may change from one orthodontist to the next orthodontist. Moreover, in some instances, the prescription is varied from the practitioner's normal practice to accommodate the initial position of a patient's tooth, the location of adjacent teeth of the patient, or the orientation of opposing teeth for a particular patient.

Orthodontic practitioners have often selected prescriptions for braces by their first-hand knowledge of past treatment results attained with other patients and by reviewing results reported in literature. However, some patients present unique problems, and reference to techniques that have been satisfactorily used in the past may not be suitable for certain patients in the future.

The problem of selecting an orthodontic prescription is aggravated by the nature of orthodontic treatment because the results of treatment may not be apparent for some time after application of the orthodontic brace to the patient's teeth. Tooth movement is carried out slowly during orthodontic therapy to reduce the amount of pain experienced by the patient and also to give sufficient time for the bone to grow and fix each tooth in place in its new position. As a result, practitioners prefer to make certain that the prescription of the brace that is initially selected is satisfactory for moving the teeth to desired, final orientations.

In addition, it is sometimes difficult for practitioners to predict the effects of tooth movements when a change in the prescription of the brace is made. The problem of predicting tooth movement is compounded by the fact that the roots of the teeth are not visible in ordinary view. Furthermore, spatial cognition of tooth movement in three dimensions is difficult, especially when such tooth movement may be influenced by the positions of adjacent teeth along the dental arch.

Generally, to achieve cost effective production of orthodontic products, such orthodontic products like brackets are designed and manufactured to average anatomy. In other words, the orthodontic brackets are not tailored to any individual anatomy of the patient. For example, a practitioner may have the ability to choose predefined and existing brackets having the following torques for an upper central tooth (0, 7, 12, 14, 17, 22).

It has been suggested that such current orthodontic products designed and manufactured to average anatomy result in orthodontists being undesirably faced with the need to select what they perceive to be brackets and archwires of the closest design to those required by a particular patient. Further, it has been suggested that use of such average anatomy orthodontic products requires later modification of the treatment of the patient.

To overcome such alleged problems, it has been suggested that custom orthodontic appliances be manufactured around the anatomy of the individual patient. As such, unlike other current orthodontic products that are designed and manufactured to average anatomy, the custom orthodontic products are manufactured and used in a tailored manner to the individual anatomy of the patient.

In providing such customization, generally, exact patient models typically derived from digitized information of anatomical shapes of the patient's mouth are used. For example, an orthodontic bracket may be automatically designed from the digitized tooth shape information and then provided using numerical controlled manufacturing technology. For example, the digitized information may be generated from measurements of the mouth of the patient, either taken directly or from a model thereof, and may include information associated with the shape of the individual teeth of the patient and/or of the patient's arches.

However, generating exact replicas of teeth is complex and costly. Likewise, designing and generating customized orthodontic products, such as brackets, from the exact replicas of the patient's teeth is also a complex and costly process. As such, digitization of a patient's teeth to provide exact models thereof along with production of customized orthodontic appliances may not necessarily be the preferred solution to providing effective orthodontic therapy.

SUMMARY OF THE INVENTION

The present invention is directed toward facilitating the selection of orthodontic brackets from predefined and existing orthodontic brackets. Generally, a user views a patient's teeth and using, for example, a user interface, a three-dimensional maloccluded tooth/arch model can be defined using three-dimensional tooth/arch model data. Likewise, a prescription is selected representative of desired final positions for the teeth of the patient. With such information, the teeth of the maloccluded tooth/arch model can be positioned in the desired final positions. Once modifications to the prescription or for that matter the patient's maloccluded tooth/arch model, if any, are made, predefined and existing orthodontic brackets can be selected, e.g., such selection can be based on selection criteria used to search a database including parameters defining such predefined and existing orthodontic brackets.

Generally, with the predefined and existing orthodontic brackets which are available today, doctors make decisions in a digital, i.e., discrete, fashion rather than in an analog fashion. For example, an orthodontic practitioner can choose the following torques for an upper central tooth (0, 7, 12, 14, 17, 22). The use of exact replicas or models of the teeth, such as by the digitization of the patient's teeth, yields exact measurements that are very representative of the patient's teeth; however, such measurements may not be all that worthwhile for the orthodontic practitioner. For example, if the exact replicas or models of the teeth provided by digitization thereof yielded, e.g., by way of a computer analysis, that a torque of 5.32 degrees would be optimum, if only predefined and existing orthodontic brackets as listed above were available, the orthodontic practitioner could only pick 0 or 7. In other words, although the exact replicas or models of the teeth provided by digitization yielded very precise information, such information still resulted in the choice of a discrete digital value, 0 or 7. In the above example, of course, the orthodontic practitioner would choose a torque of 7. Generally, such complex optimum computation and provision of exact replicas or models of teeth is a very complex and costly process.

The present invention reduces such complexity and cost by a large degree while the optimization regarding the functional process of selecting appropriate brackets is reduced only by a small factor. In other words, with definition of a three-dimensional maloccluded tooth/arch model using tooth/arch model data based on patient information, as opposed to producing and using an exact replica of the patient's teeth, e.g., an exact replica provided by digitization, a beneficial method for selecting one or more predefined and existing orthodontic brackets is provided.

A method of orthodontic appliance selection according to the present invention includes providing tooth/arch model data (e.g., individual separated three-dimensional models of teeth) and defining a three-dimensional maloccluded tooth/arch model using the tooth/arch model data as a function of patient information (e.g., patient information provided using a user interface for input of data). Further, the method includes providing prescription data representative of desired final positions for one or more teeth of the defined three-dimensional maloccluded tooth/arch model and bracket data representative of one or more parameters defining a plurality of predefined and existing orthodontic brackets. One or more of the plurality of predefined and existing orthodontic brackets are selected for use in moving one or more teeth of the defined three-dimensional maloccluded tooth/arch model to the desired final positions based on at least the prescription data.

In one embodiment of the method, one or more of the plurality of predefined and existing orthodontic brackets are selected that move the one or more teeth of the defined three-dimensional maloccluded tooth/arch model at least close to, but not necessarily exactly to, the desired final positions represented by the prescription data. The method then further includes repositioning the one or more teeth of the defined three-dimensional maloccluded tooth/arch model to positions based on at least bracket data representative of the selected predefined and existing orthodontic brackets.

In another embodiment of the method, a representation of the one or more teeth of the defined three-dimensional maloccluded tooth/arch model in desired final positions represented by the prescription data is provided, along with a representation of the one or more teeth of the defined three-dimensional maloccluded tooth/arch model as repositioned based on at least bracket data representative of the selected predefined and existing orthodontic brackets. These representations can be compared, e.g., for use in modifying the selection of the one or more of the plurality of predefined and existing orthodontic brackets.

In another embodiment of the method, archwire data representative of one or more parameters defining a plurality of predefined and existing orthodontic archwires is provided. At least one of the plurality of predefined and existing orthodontic archwires is selected for use in moving the one or more teeth of the defined three-dimensional maloccluded tooth/arch model to the desired final positions. Repositioning of one or more teeth of the defined three-dimensional maloccluded tooth/arch model may then be based on at least bracket data representative of the selected one or more predefined and existing orthodontic brackets and archwire data representative of the selected at least one predefined and existing orthodontic archwire.

In yet another embodiment, the method includes providing a representation of one or more teeth of the defined three-dimensional maloccluded tooth/arch model for a patient and providing one or more patient images representative of the patient's actual teeth (e.g., two-dimensional images and three-dimensional images) for use in comparison to the representation of the one or more teeth of the defined three-dimensional maloccluded tooth/arch model. The defined three-dimensional maloccluded tooth/arch model may be modified based on the comparison.

Even further, another embodiment of the method includes providing a representation of the one or more teeth of the defined three-dimensional maloccluded tooth/arch model for a patient and providing a representation of the one or more teeth of the defined three-dimensional maloccluded tooth/arch model in desired final positions represented by the prescription data. Such representations can be used to, for example, change patient information or prescription data resulting in a modification to the representations.

A method for use in orthodontia according to the present invention includes providing model data representative of at least one or more teeth, providing archwire data representative of at least an archwire, and providing position data defining one or more tooth positions. A representation of the one or more teeth is provided by providing a global coordinate system on a surface of the archwire and defining a local coordinate system at a facial axis point of each of the one or more teeth. The local coordinate system corresponding to each tooth is placed relative to the global coordinate system to a position defined at least in part by the position data. Thereafter, each tooth is attached to the corresponding moved local coordinate system.

In various embodiments of the method, the position data may include prescription data defining one or more desired tooth positions and/or bracket data representative of one or more parameters defining one or more orthodontic brackets. Further, a representation of orthodontic brackets with the representation of the one or more teeth may be provided in a similar manner to the placing of the teeth using the local coordinate system.

A method of orthodontic appliance selection according to the present invention includes providing tooth/arch model data for use in defining a three-dimensional maloccluded tooth/arch model and providing a user interface for allowing a user to define a three-dimensional maloccluded tooth/arch model as a function of patient information. A user interface is also provided for allowing a user to define prescription data representative of desired final tooth positions for one or more teeth of the defined three-dimensional maloccluded tooth/arch model. Further, bracket data representative of one or more parameters defining a plurality of predefined and existing orthodontic brackets is provided and one or more of the plurality of predefined and existing orthodontic brackets are selected from a database for use in moving one or more teeth of the defined three-dimensional maloccluded tooth/arch model to the desired final positions based on at least the prescription data.

Another method of orthodontic appliance selection according to the present invention includes providing tooth/arch model data representative of at least one or more teeth and defining a three-dimensional maloccluded tooth/arch model using the tooth/arch model data as a function of patient information. Prescription data representative of desired final positions for one or more teeth of the defined maloccluded tooth/arch model and archwire data representative of one or more parameters defining a plurality of predefined and existing orthodontic archwires are also provided. At least one of the plurality of predefined and existing archwires is selected for use in moving one or more teeth of the defined three-dimensional maloccluded tooth/arch model to the desired final positions. Further, bracket data representative of one or more parameters defining a plurality of predefined and existing orthodontic brackets is provided and one or more of the plurality of predefined and existing orthodontic brackets are selected for use in moving one or more teeth of the defined three-dimensional maloccluded tooth/arch model to the desired final positions based on at least the prescription data.

Further, the present invention includes computer-readable medium tangibly embodying a program executable for carrying out one or more of the functional elements described above.

The above summary of the present invention is not intended to describe each embodiment or every implementation of the present invention. Advantages, together with a more complete understanding of the invention, will become apparent and appreciated by referring to the following detailed description and claims taken in conjunction with the accompanying drawings.

BRIEF DESCRIPTION OF THE DRAWINGS

FIGS. 5B'–5B" through 5D'–5D" are diagrams for use in illustrating interaction between an orthodontic bracket and an archwire that may be taken into account when selecting orthodontic brackets according to the method shown in FIG. 4;

FIGS. 12A–12C (referred to herein as FIG. 12) are a table used for illustrating a process of selecting the predefined and existing brackets from a database such as described with reference to FIG. 11.

DETAILED DESCRIPTION OF THE EMBODIMENTS

Figure 1:
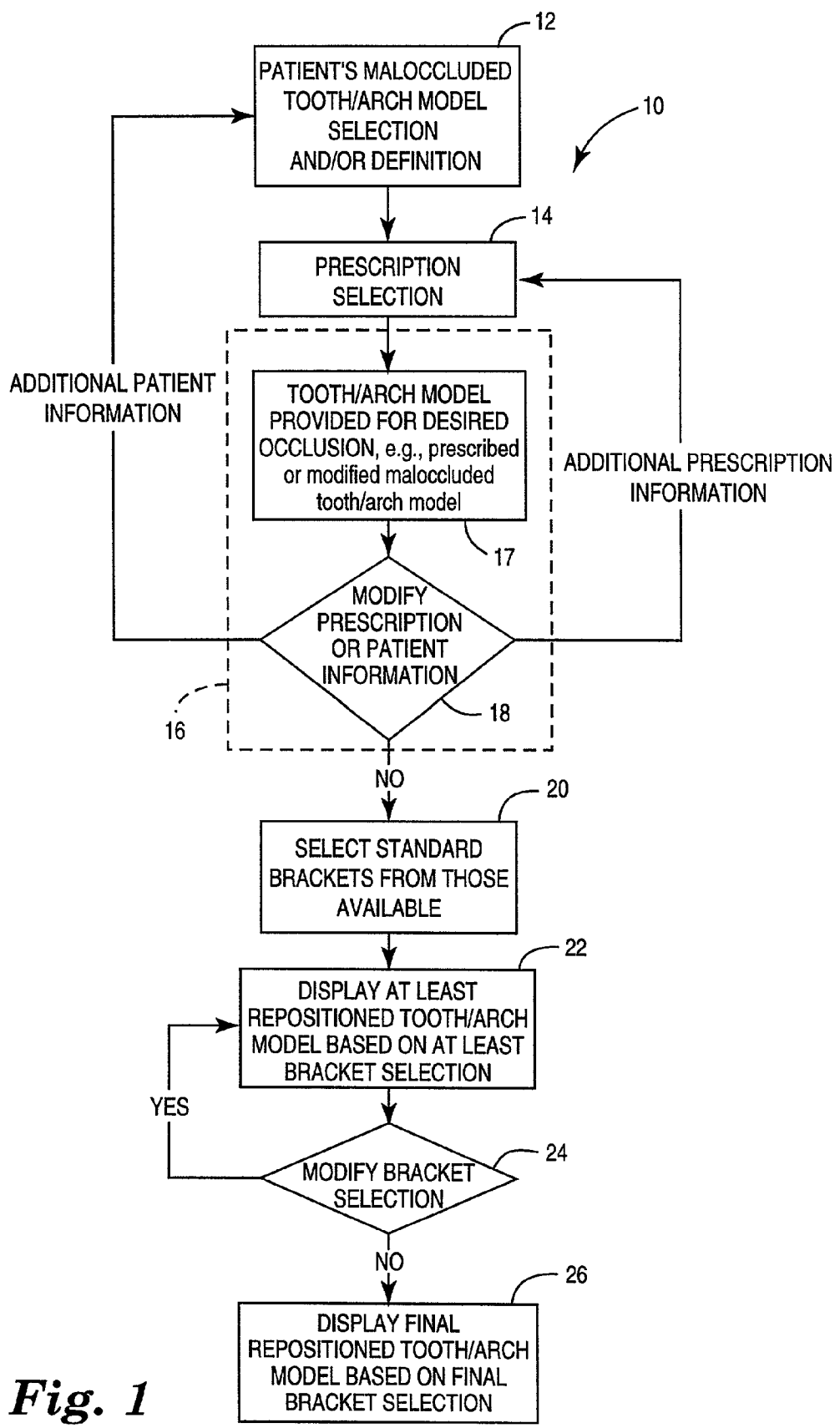
FIG. 1 is a block diagram generally showing an exemplary orthodontic bracket selection method according to the present invention.

A bracket selection method 10 according to the present invention is shown and broadly described with reference to the flow diagram shown in FIG. 1. The bracket selection method 10 generally includes patient's maloccluded tooth/arch model definition block 12 and prescription selection block 14. Patient's maloccluded tooth/arch model definition block 12 generally represents the definition by a user of a three-dimensional maloccluded tooth/arch model as a function of patient information, e.g., a patient's tooth/arch information, such as tooth size, gender, age, impression information, etc.

Generally, a maloccluded tooth/arch model refers to any model including one or more teeth that may, but do not necessarily, require movement using orthodontic therapy.

The definition of the three-dimensional tooth/arch model is preferably developed from a plurality of three-dimensional models. For example, the three-dimensional models available are provided as model data in a computer database.

The model data may be representative of one or more teeth, alone or in combination with arch information. For example, the arch information may include arch form or shape information that facilitates the selection of an archwire. The arch form by way of reference to a central plane of a corresponding selected archwire that follows the arch form (see FIG. 7), i.e., a central plane parallel to the occlusal plane, provides a reference datum for subsequent tooth and bracket positioning as described further herein.

Preferably, the three-dimensional model data is representative of separate individual teeth. Such separate individual teeth can be manipulated individually without further separation when placing them in models described herein. This is unlike the use of an actual replication of teeth, where, for example, a bite impression and later digitization is used to provide model data. In such a case, the multiple teeth digitized together must still be separated to provide individuality, and completion or provision of the entire tooth, e.g., root. For example, such digitization does not provide for root structure that is not physically represented by the impression.

Such model data may be representative of various configurations of tooth and/or arch models created by, for example, imaging and/or recording actual patient teeth and providing an average common representation thereof. For example, the three-dimensional models may be defined by or correspond to various patient criteria such as gender, age, race, tooth size, arch size, arch shape, etc. As such, a user interface provided to a practitioner may allow the input of various patient information. Such patient information can then be used to search a database defining the models to result in the selection of a best match three-dimensional model data from the plurality of available three-dimensional models provided by the model data in the computer database.

The patient's maloccluded tooth/arch model may be defined by the user through selection of an arch form, individual teeth, groupings of an arch form and teeth, groupings of multiple teeth, or through selection of any other model data representative of one or more teeth and/or arch forms. Preferably, an arch form and individual teeth are selected for definition of the patient's maloccluded tooth/arch model based on user input of patient information.

The prescription selection block 14 is generally representative of the user selecting prescription data from multiple available prescriptions representative of desired final positions for one or more of the teeth of the maloccluded tooth/arch model defined for a patient. The multiple available prescriptions may be provided by prescription data in a computer database. The prescription for each patient/tooth can be selected on an individual basis or as a group.

The selected prescription data representative of desired final positions for one or more of the patient's teeth is not limited to the choice of one or more predefined bracket prescription systems. In other words, the prescription data representative of desired final positions for one or more of the patient's teeth is not the same as the prescription information that is representative of one or more parameters of predefined and existing orthodontic brackets to be selected according to the present invention. For simplicity, and to eliminate confusion between the selected prescription data representative of desired final positions for one or more of the patient's teeth versus prescription information that is representative of one or more parameters of predefined and existing orthodontic brackets, the prescription information that is representative of one or more parameters of predefined orthodontic brackets will be referred to herein and in the claims as bracket data.

With a defined three-dimensional maloccluded tooth/arch model (block 12) and a selected prescription (block 14) being provided, a tooth/arch model having the desired occlusion for the teeth of the patient can be achieved (block 16) by providing the teeth of the three-dimensional maloccluded tooth/arch model defined by the user in the desired prescribed positions (block 17). The user can then determine if these final positions are actually desired for the teeth or if modifications need to be made (block 18).

For example, with such a representation of the patient's teeth in desired final positions shown to the user, the user may optionally modify prescription or patient information as represented by block 18 and the loops back to block 12 and 14. Although not necessary for completion of the bracket selection method 10, such modification of the prescription or patient information (block 18) may provide a better representation of the teeth of the patient's maloccluded tooth/arch model positioned as prescribed by the selected prescription, and as such, may provide for a better selection of brackets from predefined and existing orthodontic brackets (block 20), e.g., a bracket selection that moves the maloccluded teeth closer to the prescribed positions.

Block 20 of the bracket selection method 10 is generally representative of the selection of standard brackets, i.e., predefined and existing orthodontic brackets, from a plurality of predefined and existing orthodontic brackets defined by one or more parameters representative thereof in a computer database. At least one archwire corresponding to the arch form defined for the patient may also be selected from a plurality of predefined and existing archwires. The selection of the predefined and existing brackets is, in many circumstances, affected by the interaction between the archwire and the brackets when moving the maloccluded teeth of the model into the desired final positions as defined by the prescription data. As such, this interaction should be considered as further described below in the selection of the predefined and existing brackets.

Such selection of predefined and existing orthodontic brackets (block 20) may be performed in any number of manners. For example, such selection may be performed by the user entering bracket selection criteria via a user interface, e.g., based on the selected prescription. Such bracket selection criteria is used in a search of a database providing the bracket data representative of one or more parameters defining the plurality of predefined and existing orthodontic brackets such that selected brackets, i.e., best match brackets or brackets that will best move the maloccluded teeth into the prescribed desired positions, result from the search. The bracket selection criteria is generally representative of at least the prescription data selected by the user or otherwise defined by the user (block 14) and the defined maloccluded tooth/arch model (block 12).

Further, for example, such selection of predefined and existing orthodontic brackets may performed by the system searching the database using the angulation, in/out, or other prescription data selected by the user (block 14). Yet further, such selection may be performed by taking into account one or more other parameters such as torque loss (see FIG. 11B).

Yet further, multiple iterations of a combination of one or more different selection processes described herein may be used to select the brackets that will best move the maloccluded teeth into the prescribed desired positions. For example, a first cycle of selection may be performed by the system based only on the selected prescription data (e.g., the selected prescription data being the bracket selection criteria) defining the desired positions for the teeth of the maloccluded model, with a second cycle performed using additional user entered bracket selection criteria to further modify the selection process. The combinations of processes used to select the brackets are numerous and one skilled in the art will recognize that each and every possible combination is not listed specifically herein but that such combinations are clearly within the scope of the present invention.

Upon bracket selection, the teeth of the maloccluded model are repositioned based on the bracket data (i.e., bracket prescription information) representative of the selected orthodontic brackets (block 22). In other words, the bracket data representative of parameters of the selected predefined and existing brackets is used to modify the position of one or more teeth of the patient maloccluded tooth/arch model.

The selection process of block 20 may not result in an exact match with the selected prescription for the desired final tooth positions. In other words, the teeth of the patient maloccluded tooth/arch model will most likely only be moved close to, but not necessarily exactly to, the desired final positions as represented by the selected prescription of block 14.

The repositioned teeth (block 22) may be displayed to the user. The maloccluded teeth repositioned based on the bracket data may be displayed alone or in conjunction with other defined models (e.g., the maloccluded tooth/arch model for the patient, the maloccluded teeth moved into the desired final positions based on the selected prescription data, other image data, etc.). This presents the user with an opportunity to view the results of the selected orthodontic brackets and have the ability to modify the bracket selection (block 24) or any other parameter requiring redefinition to achieve a more effective orthodontic bracket selection. The teeth may then be repositioned again using the bracket data of the new or modified selection. This modification and repositioning process can be repeated until a suitable final position for the teeth is attained as represented by the loop between blocks 24 and 22. One will recognize that this modification process may never achieve the desired positions of the selected prescription data of block 14.

Once a suitable final position for the teeth of the maloccluded tooth/arch model is attained, a display of the final tooth model with or without brackets based on the final selection of predefined and existing orthodontic brackets is provided (block 26).

With reference to block 12, the model data representative of a plurality of three-dimensional tooth/arch models may include model data representative of a full set of teeth or one or more individual teeth with one, both, or partial arches. A user may select the patient's tooth/arch model data from a library of data. For example, if a user enters various patient information, one or more three-dimensional tooth/arch models may be displayed for a user, e.g., practitioner, to review and modify as appropriate.

Likewise, user-entered data may result in the program displaying a selection of matches in thumbnail images, e.g., teeth which match the patient information supplied by the user. Thereafter, the user may click on selections, e.g., particular teeth, and build a three-dimensional model and fine tune the model if desired.

In other words, the model data representative of the plurality of three-dimensional tooth/arch models may be either representative of individual teeth or multiple teeth. However, in all of such cases, according to the present invention, with respect to at least the selection of brackets, the model data is not an actual model of the patient's actual teeth, but is representative of the patient's teeth.

Preferably, the model data is representative of individual teeth and/or arch forms that may be selected by the user to define the maloccluded tooth/arch model for a patient. Such model data may be provided by using actual three-dimensional models to generate a computer tooth library, e.g., a tooth library including teeth for various tooth positions. However, the present invention is not limited to any particular manner of providing the model data.

Further, the model data representative of the teeth may be provided by use of data for a model tooth that is scaled in dimensions as needed to relative dimensions corresponding to the patient's tooth. For example, data representing a tooth model may be obtained from the library of teeth. The data may then be changed as needed to increase or decrease the size of the tooth model along one or more reference axes until the tooth model is similar in size and/or shape of the corresponding tooth of the patient.

The scaling operation, i.e., the manipulation of the data to increase or decrease the size of the model tooth along one or more axes, may be carried out by the user through the input of numerical data from measurements of the patient's actual tooth or a relative ranking of the size of the patient's actual tooth. If the selection method includes the optional step, as described below, of including digitized images of the patient's actual teeth, scaling may be carried out by the user through visual comparison of the image of the model tooth to the appearance of the patient's actual tooth. The scaling process may be carried out for each tooth in the dental arch as needed. For example, the scaling operation may be performed by selecting and dragging a border or surface of the tooth being scaled.

The estimated models of teeth selected by the user utilized according to the present invention are sufficiently close to the patient's actual teeth such that an exact replica of the patient's teeth is unnecessary in the bracket selection method 10. As indicated previously, using such computer-generated model teeth as opposed to using digitized representations of a patient's actual teeth, reduces the complexity and cost of attempting to provide an exact model or replica of the patient's actual teeth. Further, as previously described herein, the individual nature of the teeth provide a far less complex process of providing separated teeth that can be easily manipulated, as opposed to capturing an actual representation of the teeth and then further needing to perform complex algorithms to separate the teeth captured into individual separated teeth.

The bracket selection method 10 according to the present invention is used to select predefined and existing brackets that are defined by certain bracket data. The bracket data, i.e., orthodontic bracket prescription information, representative of parameters of predefined and existing orthodontic brackets and used in the selection process described herein may include values representing the torque, angulation, and rotation provided by the bracket. The bracket data may also include an "in/out" value which may represent, for example, the shortest distance between the lingual side of the archwire slot and the outwardly facing side of the bracket base that is intended to contact or be closely adjacent the surface of the patient's tooth. Bracket data may also include other aspects such as labial-lingual depth of the archwire slot, the occlusal-gingival width of the archwire slot, and the mesial-distal length of the archwire slot. The bracket data may also optionally include the material of the bracket and/or the material of the structure defining the archwire slot (such as an archwire slot liner), and the type or classification of appliance (e.g., a "Begg" bracket, a twin bracket, or a bracket with rotation wings). The bracket data may also include linear and/or angular tolerances of the various dimensions and angulations.

The bracket selection method 10 may also be used to select predefined and existing archwires that are defined by certain archwire data. The archwire data representative of parameters of predefined and existing orthodontic archwires and used in the selection process may include values that represent the shape of the archwire, such as the cross-sectional shape (e.g., round, rectangular, or square) as well as its overall shape when in its normally relaxed configuration (e.g., whether it lies in a flat plane when relaxed or whether it is constructed to have a reverse curve of Spee when relaxed). Moreover, the archwire data for the archwires may include overall dimensions when relaxed as well as its cross-sectional dimensions (e.g., its diameter for an archwire having a round cross-sectional configuration, and its width and depth for archwires having a rectangular cross-sectional configuration). Further, the archwire data may also include its composition, stiffness, and/or values representing frictional characteristics of the archwire in use.

As used herein, the word "bracket" may include any orthodontic brackets and also orthodontic tubes, such as buccal tubes. Buccal tube brackets are typically mounted on the patient's molar teeth and receive ends of the archwire. Optionally, the buccal tubes are convertible. In convertible tubes, the tubular passage may be "opened" by the practitioner when desired to create a slot that is open along one side, such as along its buccal side. In some circumstances, buccal tubes are welded to metallic orthodontic bands that are placed around the molar teeth to provide a stable base for mounting the buccal tubes. Orthodontic bands may be selected and applied as described, for example, in U.S. Pat. No. 6,089,868 issued 18 Jul. 2000 entitled, "Selection of Orthodontic Appliances."

Figure 2:
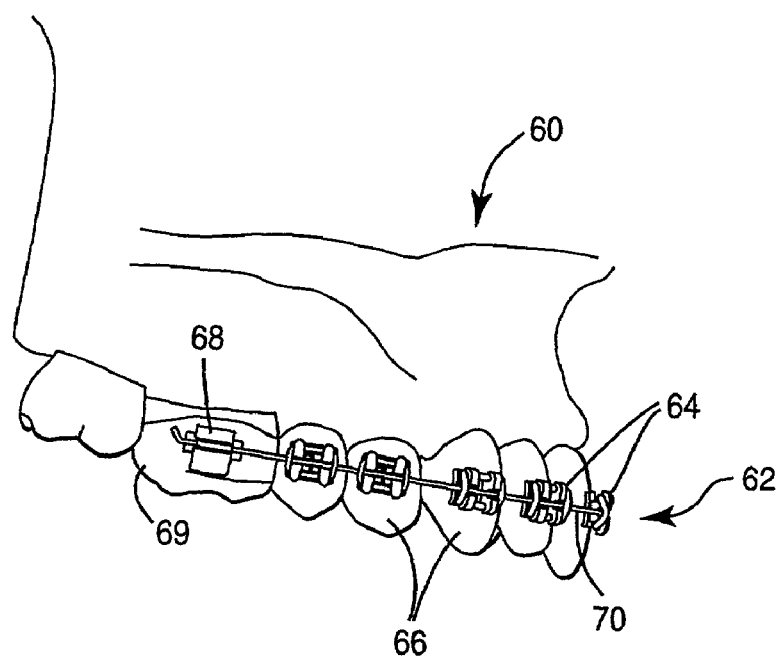
FIG. 2 is a side elevational view of an example of an orthodontic brace including a number of brackets along with an archwire received in the slots of each bracket.

An example of a system of brackets and archwires is shown in FIG. 2. In FIG. 2, a dental arch 60 of a patient is shown along with a first brace 62. The first brace 62 includes a set of brackets 64, each of which is bonded to a respective tooth 66 of the dental arch 60. Buccal tube brackets 68 are mounted on molar teeth 69 of the dental arch 60. The brackets 64, 68 have slots or grooves that receive an archwire 70. Although only an upper dental arch is depicted in FIG. 2, it should be understood that in this regard a brace similar to brace 62 may be affixed to the patient's lower dental arch as well.

The archwire 70 is secured to the brackets 64, 68 by ligating structure, such as wire ties or the tiny elastomeric O-rings shown in FIG. 2. Alternatively, the bracket 64, 68 may be of the type known as "self-ligating" brackets that include sliding clips, shutters, or other types of latches to retain the archwire 70 in place. The archwire 70 forms a track to guide movement to the bracket 64, 68 as well as the associated teeth toward prescribed positions as selected by the practitioner.

Figure 3:
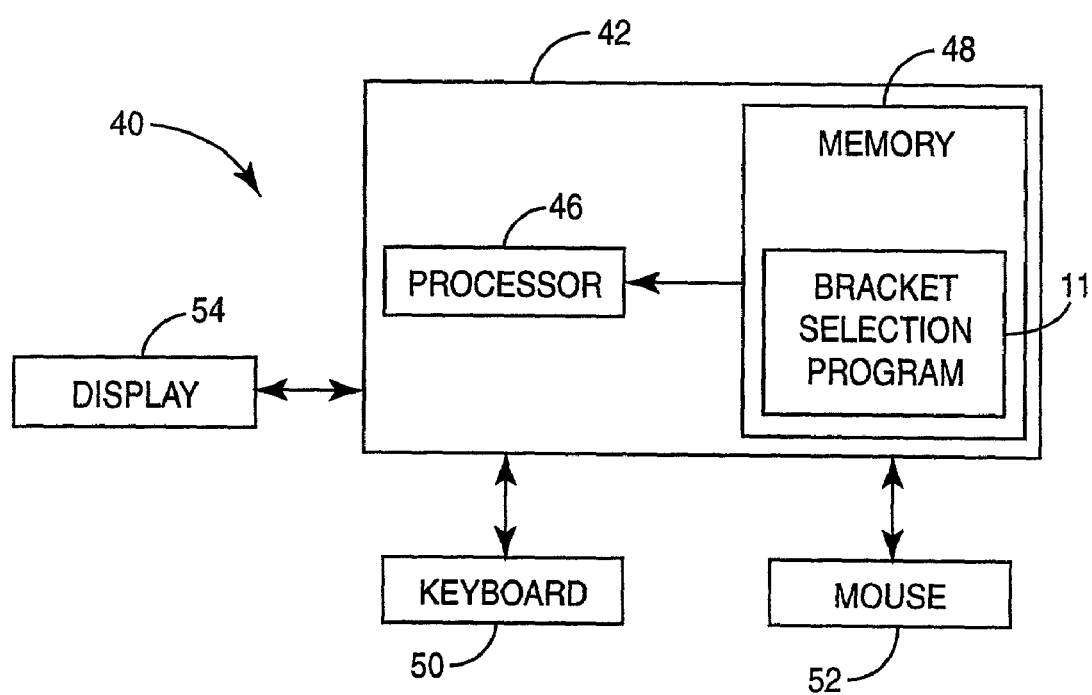
FIG. 3 is an orthodontic appliance selection system employing an orthodontic bracket selection program in accordance with the present invention.

As shown in FIG. 3, a selection program 11 for performing the bracket selection method 10, or at least portions thereof, is resident in memory 48 of a computing unit 42 of an orthodontic appliance selection system 40. The computing unit 42 further includes processor 46. Further, the data representative of the various elements of the present invention, e.g., the one or more prescriptions, the plurality of three-dimensional tooth/arch models, the data representative of one or more parameters defining a plurality of predefined and existing orthodontic brackets, etc., may also be resident in memory 48 for use by program 11. Alternatively, such data may be provided as inputs to computing unit 42 by a user or by some other peripheral device for use by program 11 or for storage in memory 48.

It will be readily apparent to one skilled in the art that the present invention may be adapted to be operable using any bit processor-based system, e.g., a personal computer, and, further, that the present invention is in no manner limited to any particular processing system. The amount of memory of the system should be sufficient to allow for operation of the program 11 and storage of data, such as model teeth data and prescription data, for use by program 11. It is readily apparent that such a memory may be provided by peripheral memory devices. The system 40 may include any number of other peripheral devices as desired for operation of the system 40, such as, for example, the following respective devices: display 54, keyboard 50, and mouse 52. However, one skilled in the art will recognize that the system is in no manner limited to use of such devices, nor that such devices are necessarily required for operation of the system 40.

For example, computing system 40 may be a Net Power Semetra-II with a true-TX graphics card. However, any suitable computing system may be used. Various programs and languages may be used to accomplish the functions as described herein, as would be readily apparent to one skilled in the art. For example, such functionality may be provided using C++ language, Open GL, etc. Further, available software packages may be used for providing various functions, such as display of images, manipulation of images, etc. For example, Open Inventor available from Silicon Graphics may be used to display images, and Digital Diagnostic Protocol may be used to communicate the information.

More detailed illustrative embodiments of the bracket selection method 10 according to the present invention are shown by the tooth movement and bracket selection method 100 and embodiments thereof as shall be described with reference to FIGS. 4–12.

The bracket selection method 100 includes block 112 representative of a user entering patient information for use in the definition of a three-dimensional maloccluded tooth/arch model for a patient. Preferably, the present invention includes a user interface which instructs the user to provide certain types of patient information (block 140).

For example, the patient information may include any information that is pertinent to or which leads to distinguishing characteristics of teeth or arches of a patient. For example, such patient information may include the patient's gender, age, race, or any other type of information descriptive of a group of patients that is useful in defining an estimated tooth/arch model. Generally, by providing group-type information representative of the patient, certain sizes and tooth shapes can be selected. Further, for example, patient information may include tooth size such as from a scale of 1–5, arch size such as from a scale of 1–5, and arch shape (e.g., Orthoform 1, 2, and 3). This patient information may also be bite impression information taken directly from a patient by the user of the bracket selection system described herein.

Upon entering of such patient information, the computer program, e.g., computer program 11, searches for tooth and arch models from a tooth/arch model database (block 142). The tooth/arch model database, as described previously, may include model data representative of one or more teeth, either individually or in combination, whole or partial arch models, combination tooth and arch models, or any other three-dimensional models including tooth and/or arch information. Separate tooth and arch models may be stored as a library file in the tooth/arch model database. Further, preferably, after entry of such patient information, various tooth models and arches are provided for viewing by a user and the user is allowed to select one or more tooth models and arch models to estimate the patient's teeth/arch configuration. As described further below, such a selection may be modified if desired.

As described previously, scaling may be used to define the teeth of the maloccluded tooth/arch model. Further, an arch form may be defined by scaling. In this option, the shape of the generic arch form is increased or decreased along one or more references axes until reaching the shape desired by the user. Scaling of the arch form may be carried out by any one of a number of methods. For example, a model of the patient's arch form may be created and measured at certain reference points, and the generic arch form can then be scaled as needed. The arch form may be scaled from a single arch form, or may be scaled from one of a number of generic arch forms that are retained in a data file containing a library of arch forms.

With further reference to block 112 for defining the maloccluded tooth/arch model, the teeth of the maloccluded model may be placed in the defined positions, and the user may view such teeth on the display (block 144) to determine whether the displayed maloccluded teeth satisfy the user's expectations. If the user is satisfied with the displayed maloccluded teeth, then the user can move forward and select prescription data for such teeth as shown in block 114.

The maloccluded teeth may be placed in positions in the maloccluded tooth/arch model in a manner such that they best match the patient's maloccluded teeth. For example, a representation of the one or more teeth of the defined three-dimensional maloccluded tooth/arch model for a patient may be provided by moving each tooth to a position that matches, as close as possible, the position of the corresponding tooth of the patient or, for example, models formed of multiple teeth may be chosen wherein little positioning of individual teeth is required.

If the user is not satisfied with the teeth in the defined maloccluded tooth/arch model, then the maloccluded model may be changed (block 152). For example, patient information may be changed to reselect teeth. In other words, information concerning the patient may be changed such that the maloccluded model teeth or the arch form is changed and through the previous process described herein displayed to the user in a changed form.

To assist the user in making changes to the maloccluded tooth/arch model, patient two-dimensional digitized images (block 148) or patient three-dimensional digitized images (block 150) may be overlaid with the maloccluded tooth/arch model on the computer display (block 146). This would allow the user to fine tune the displayed maloccluded model teeth such that the estimated teeth representative of the patient's teeth are as desired by the user. Clearly, use of digitized two-dimensional or three-dimensional images is only a supplemental tool that may be used optionally in the present invention.

In another embodiment of the definition of the three-dimensional maloccluded tooth/arch model, information (e.g., full bite impression information or digitized representations) of the patient's actual teeth may be used for providing a full arch model representation of the patient's teeth. However, the separate individual selected model teeth, e.g., complete with root, are placed in the full arch model for the patient. As such, this embodiment makes use of actual patient information while still reducing the complexity and cost of attempting to provide an exact model or replica of each of the patient's actual teeth. In other words, the individual nature of the model teeth, i.e., individual separated teeth, is used in combination with a model created from information more closely defining the actual patient. Therefore, a partial capture of the patient's actual configuration is used, while the need to perform complex algorithms to separate the teeth captured (e.g., by impression or digitization) into individual separated teeth is eliminated.

Figure 4A:
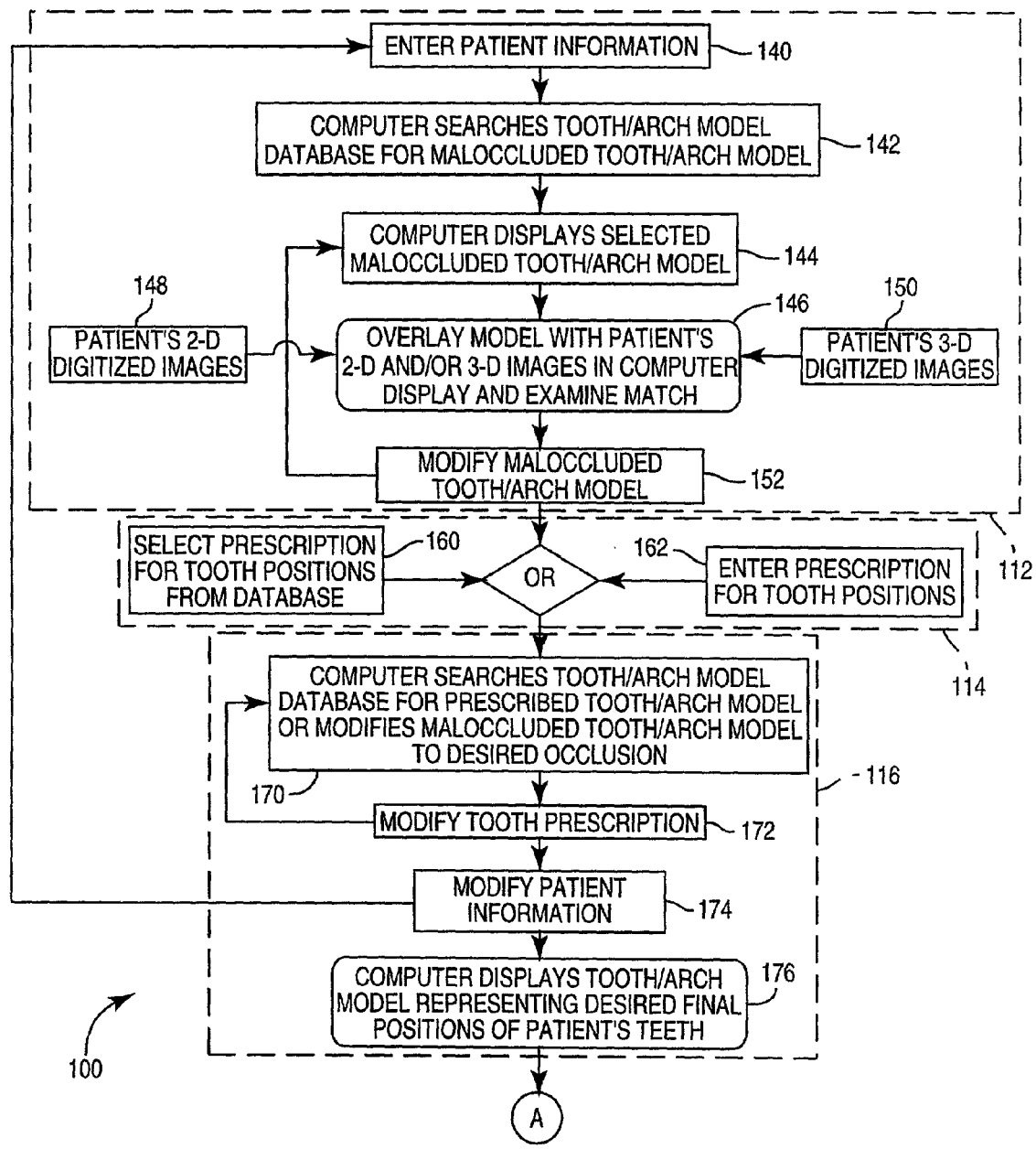
FIG. 4 is a block diagram illustrating one embodiment of the orthodontic bracket selection method of FIG. 1.

With the three-dimensional maloccluded tooth/arch model being defined (block 112), prescription data representative of desired final positions for the teeth of the maloccluded model can be selected or otherwise defined (block 114). As shown in FIG. 4, prescription information can be provided to the computer program in multiple ways.

Block 160 allows a user via a user interface to select a standard prescription for tooth positions from one or more prescriptions stored in a database. For example, known prescription values are commonly used for tooth positions according to known techniques. Examples of well-known techniques include those taught by Drs. McLaughlin, Bennett, and Trevisi (the "MBT" brand bracket prescription), those taught by Dr. Ron Roth, and those taught by Dr. Lawrence F. Andrews.

Further, the prescription information may be provided by the user through an additional user interface that allows the user to enter various prescription parameters such as in/out, angulation, and torque for each tooth (block 162). Such modification provides the user, e.g., an orthodontist, the ability to achieve positions for the model teeth corresponding to the prescription that cannot be achieved with a standard prescription.

Figures 4B, 5A:
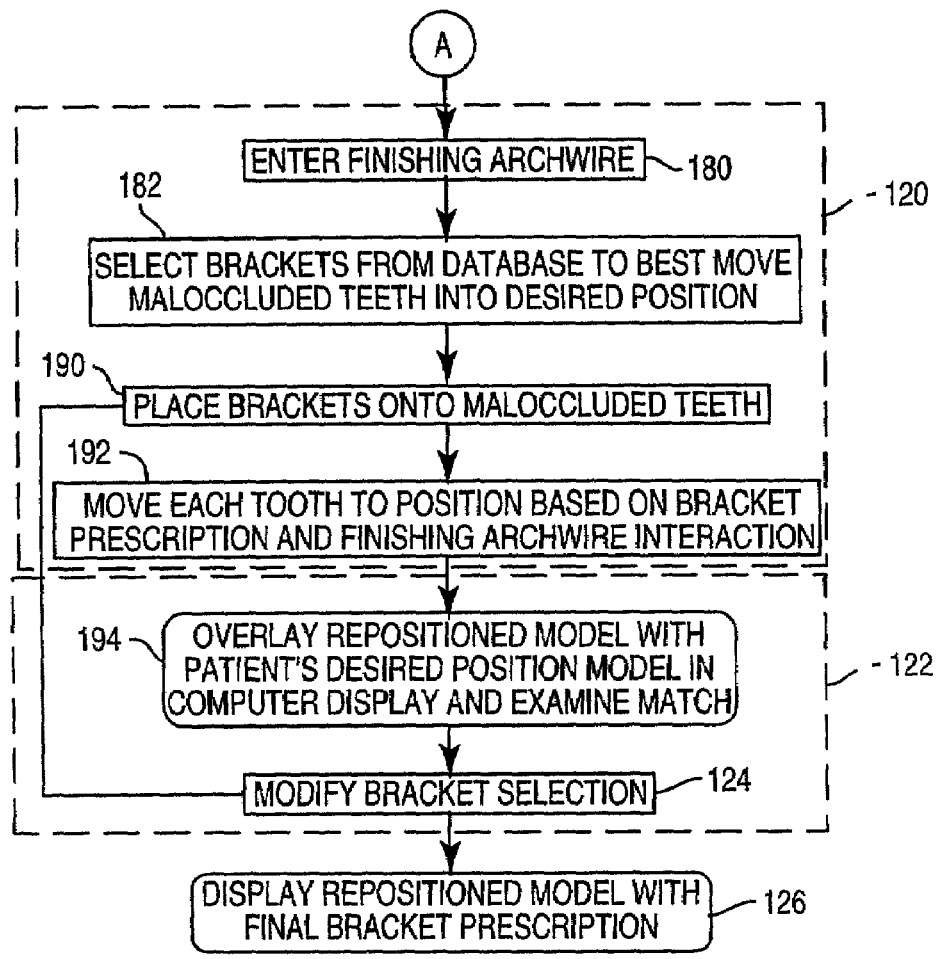
FIG. 5A is a table illustrating a prescription that may be selected according to the method shown in FIG. 4.

FIG. 5A shows a typical prescription from L. F. Andrews, "Straight Wire, the Concept and Appliance", L. A. Wells (1989). The in/outs were calculated from subtracting crown prominence of each tooth from 3.5 millimeters. The prescription 170 is just one of many different types of prescriptions that may be stored in a library database and selected by a user via a user interface provided by program 11.

With the prescription data selected, and/or otherwise defined, (block 114), the method 100 proceeds to place the maloccluded teeth of the patient according to the desired final tooth positions corresponding to, or prescribed by, the selected prescription and, optionally modify the model resulting from such placement (block 116). One exemplary implementation of a tooth positioning process (block 170) for positioning the maloccluded teeth to the desired or prescribed occlusion is shown in the flow diagram of FIG. 6. However, it will be apparent that any method of placing the teeth or moving the teeth to the desired positions may be used according to the present invention.

Further, the process may include searching a tooth/arch model database for a prescribed tooth/arch model as opposed to modifying the positions of the maloccluded teeth into the desired final positions. Such position modification of the maloccluded teeth may include positioning each of the teeth selected for the maloccluded model to the desired prescribed occlusion. Alternatively, a local coordinate system already created for the teeth of the maloccluded model may be repositioned and each tooth reattached thereafter.

Figure 6:
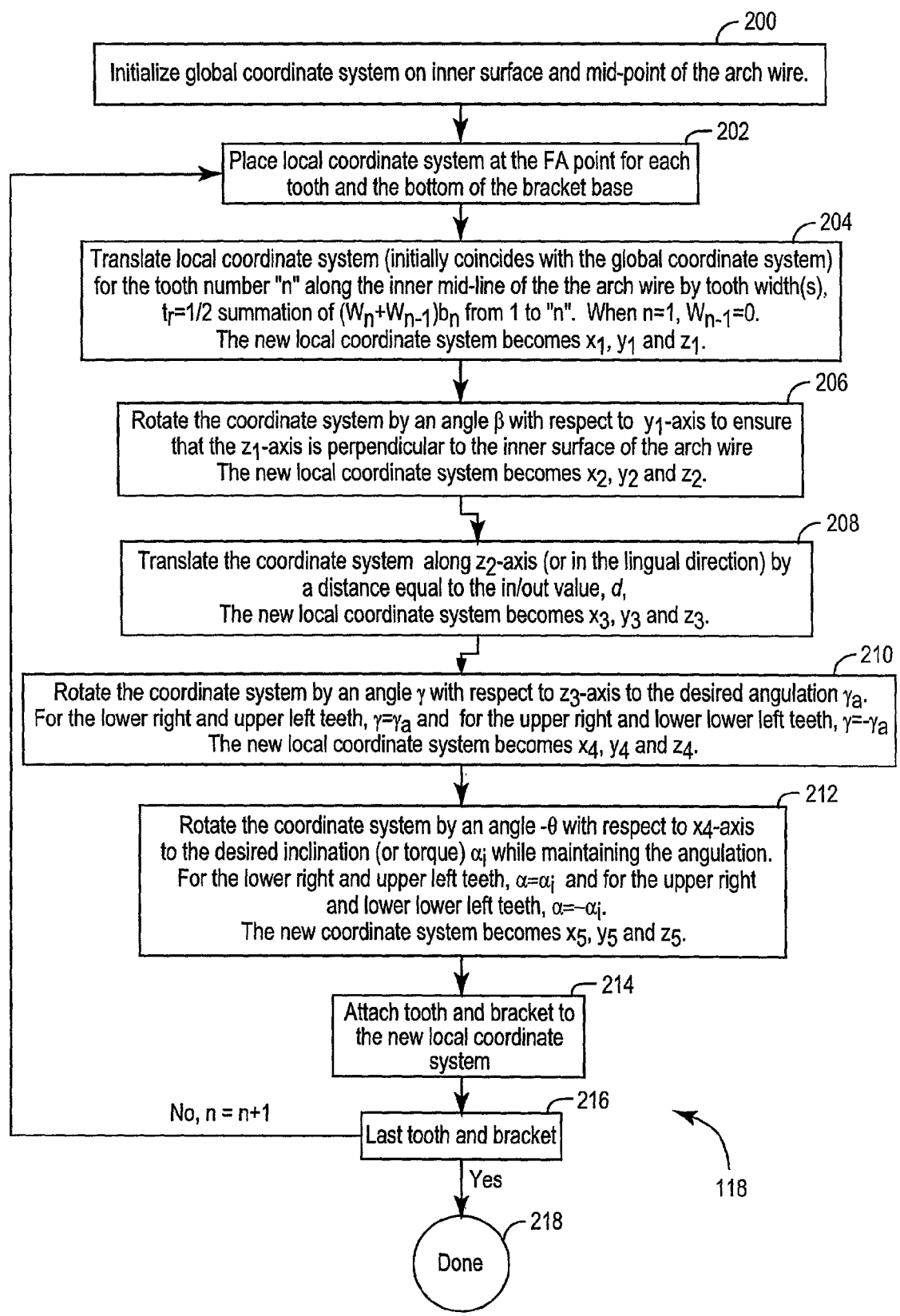
FIG. 6 is a block diagram of one illustrative embodiment of a process for placing teeth, and likewise brackets, of a tooth/arch model to certain positions, such as shown generally in FIG. 4.
Figure 7A:
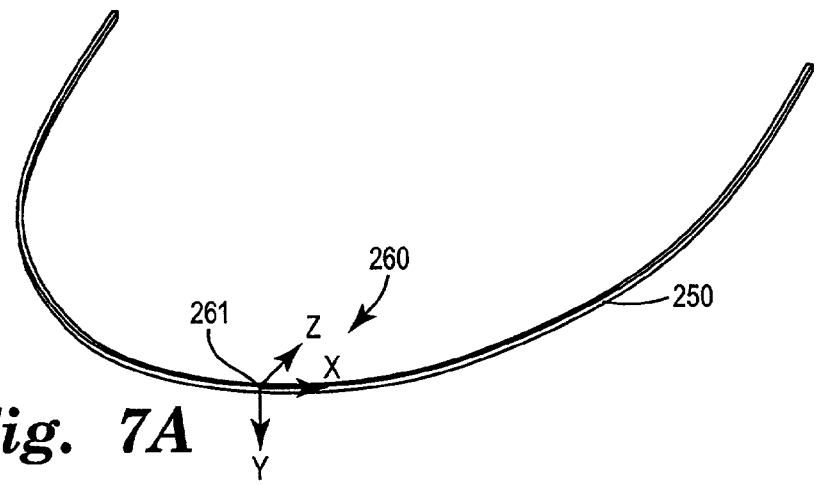
FIGS. 7A–7C are used to generally illustrate the embodiment of the process shown in FIG. 6.
Figure 7B:
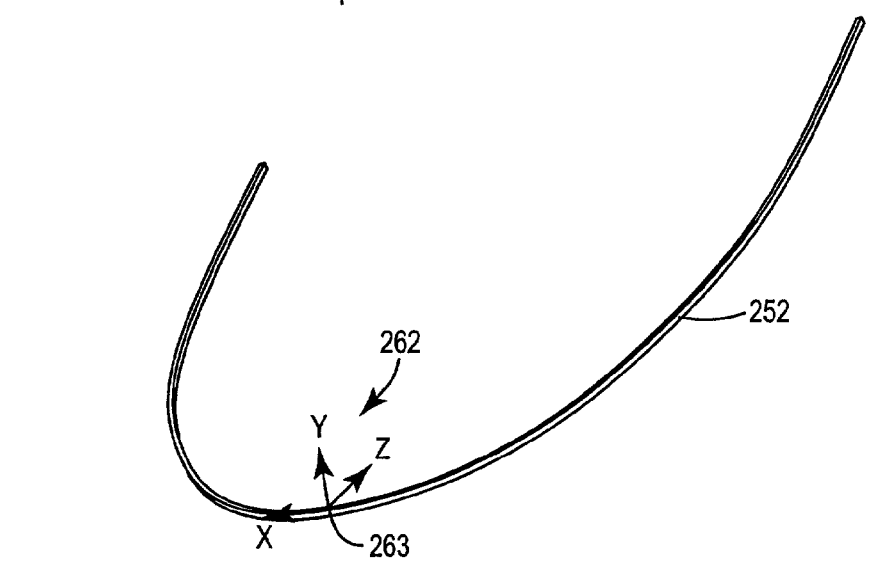

One illustrative tooth positioning process 118 for providing a representation of the one or more maloccluded teeth based on the selected prescription data representative of the desired final positions for the teeth is shown in FIG. 6 and can be generally described with reference to FIGS. 7A–7C. FIGS. 7A and 7B are representative of upper archwire 250 and lower archwire 252 corresponding to defined arch forms defined for the patient in the definition of the maloccluded tooth/arch model.

According to the tooth placement process 118 for moving teeth to prescribed tooth positions, the method is initialized by positioning a global coordinate system on an inner surface of the archwire and at the midpoint of the archwire (and at the central plane thereof). For example, as shown in FIG. 7A, global coordinate system 260 is positioned with its origin 261 on the inner surface and midpoint of the upper archwire 250. Likewise, as shown in FIG. 7B, global coordinate system 262 is initialized with its origin 263 on the inner surface and midpoint of the lower archwire 252.

Figure 7C:
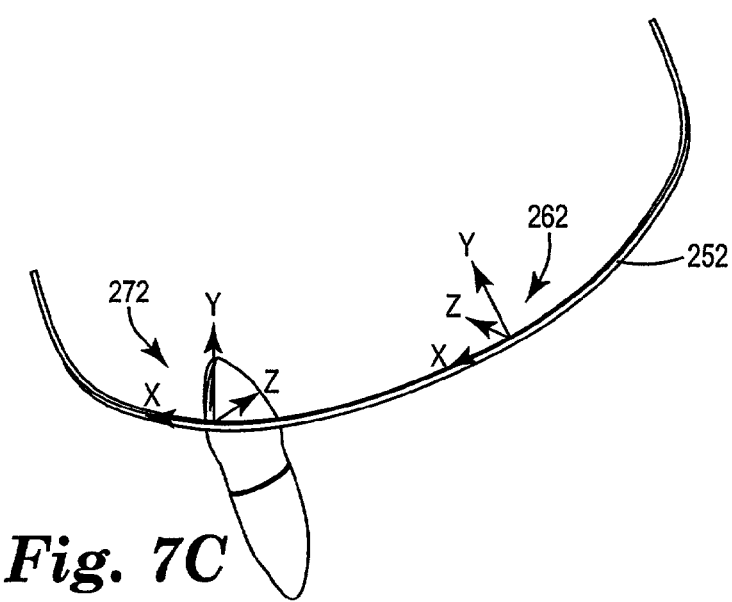

Further, generally, the tooth placement process 118 includes moving a local coordinate system 272 associated with a tooth relative to the global coordinate system 262 of archwire 252 to a prescribed position as shown in FIG. 7C. Thereafter, preferably, tooth 270 is then attached to the local coordinate system 272. Likewise, all the other model teeth (if any) of the lower arch 252 are moved in the same manner to the prescribed positions. For simplicity, only descriptions relative to the lower arch 252 shall be provided herein. However, via symmetry, substantially the same process applies to the upper arch 250.

A more detailed description of the tooth placement process 118 shown in FIG. 6 shall further be described with reference to FIGS. 8 and 10A–10F. As shown in block 200, a global coordinate system 262 is initialized on the inner surface 267 and midpoint 269 of the archwire 252 as shown by the global coordinate system 262 having its origin at the inner surface 267 and midpoint 269 of archwire 252 shown in FIG. 10A. Generally, orthodontic archwires, for example, are often sold according to standardized shapes that have been developed over the years. Archwires typically appear as a smooth curve that is symmetrical on either side of a midpoint, but the radius of the curvature of the archwire typically varies along the length of the archwire. The global coordinate system 262 as described herein is generally tangent to the inside (lingual side) of the archwire at its midpoint in the mesial-distal direction, and is parallel and normal to the occlusal plane.

Generally, the computer program automatically creates the global coordinate system on the archwire 252. For example, in one embodiment, data representative of the surface of the archwire, or at least approximately representative of the archwire surface, is created if it does not yet exist in the model data, e.g., an archwire that follows the arch form. The surface of the archwire could be provided by data of a solid model, wire frame data, data representing the surface, or data representing a point cloud surface. Preferably, the archwire follows the arch form defined for the patient (block 112). With the archwire 252 defined as illustrated above, the global coordinate system 262 is positioned with its origin on the inner surface 267 of the archwire and at the midpoint 269 of the archwire 252.

Figure 8:
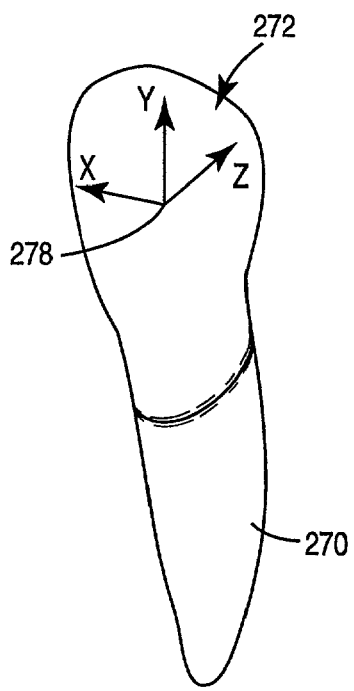
FIG. 8 is a perspective view of a tooth showing an illustrative local coordinate system as described and utilized in the process of FIG. 6.

With the provision of the global coordinate system 262 as shown in block 200 and in FIG. 10A, a local coordinate system 272 for each model tooth is then moved as further described below. Each tooth is later attached to the corresponding local coordinate system with its origin at the facial axis (FA) point 278 of each tooth. One example of the attachment of the local coordinate system 272 is shown in FIG. 8. FIG. 8 illustrates the attachment of local coordinate system 272 at the FA point 278 of the tooth 270. The z axis of the local coordinate system 272 is perpendicular to the crown surface while the y axis and the x axis are tangent to the crown.

Figure 10A:
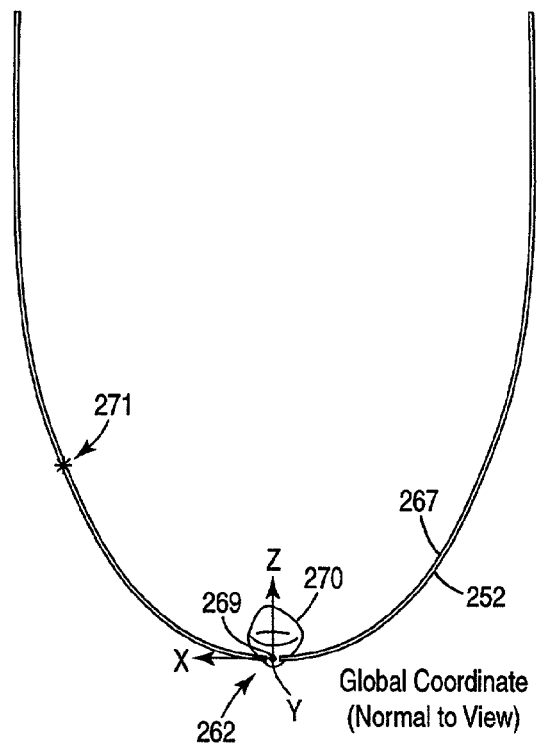
FIGS. 10A–10F further illustrate in detail one illustrative embodiment of placing a tooth according to the process described with reference to FIG. 6.
Figure 10B:
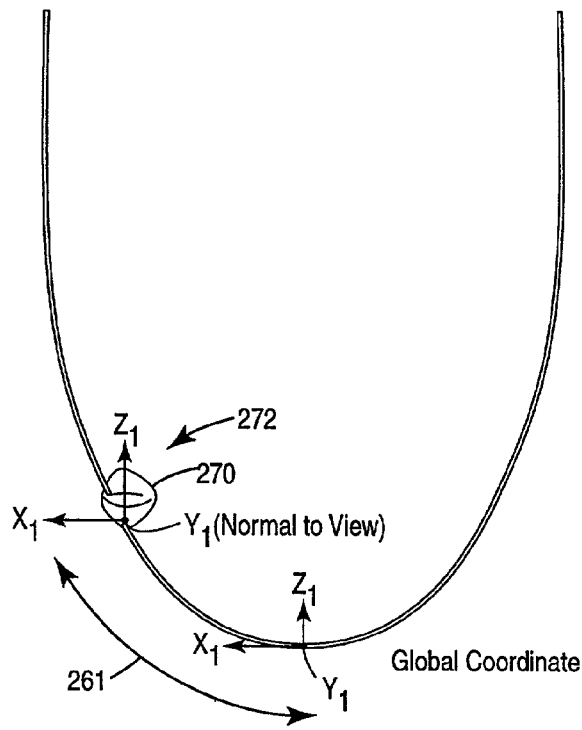

The local coordinate system 272 which may initially coincide with the global coordinate system 262 as shown in FIG. 10A is then translated along the inner midline of the archwire by tooth widths (block 204). In other words, depending upon the tooth number "n," i.e., the number corresponding to the teeth lying to one side of the midpoint of the archwire, the local coordinate system 272 for the tooth number "n" is translated a distance 261 along the inner midline (i.e., midline lying in the central plane) of the archwire 252 to a point 271 by tooth widths, $$t_r = \frac{1}{2}\sum_{1}^{N}(W_n + W_{n-1})b_n$$

from 1 to "n" as shown in FIG. 10B. When n=1, $W_{n-1}$=0. "$b_n$" is a factor greater than one or smaller than one to account for the larger (or smaller for lingual arch) arch radius of the archwire than the crown prominence arch on which the tooth widths are measured. After translation, the local coordinate system becomes $x_1$, $y_1$, and $z_1$, where $y_1$ is normal to the view shown in FIG. 10B.

Figure 10C:
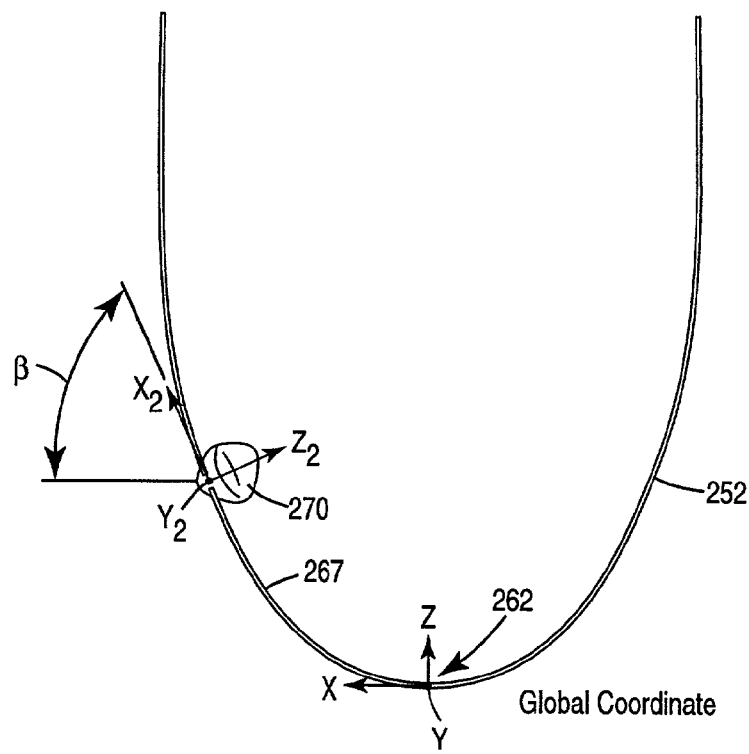

Thereafter, per block 206, and as shown in FIG. 10C, the local coordinate system $x_1$, $y_1$, $z_1$, is rotated by an angle beta ($\beta$) with respect to the y axis to ensure that the $z_1$-axis is perpendicular to the inner surface of the archwire 252. The new local coordinate system resulting from the rotation becomes $x_2$, $y_2$, $z_2$.

Figure 10D:
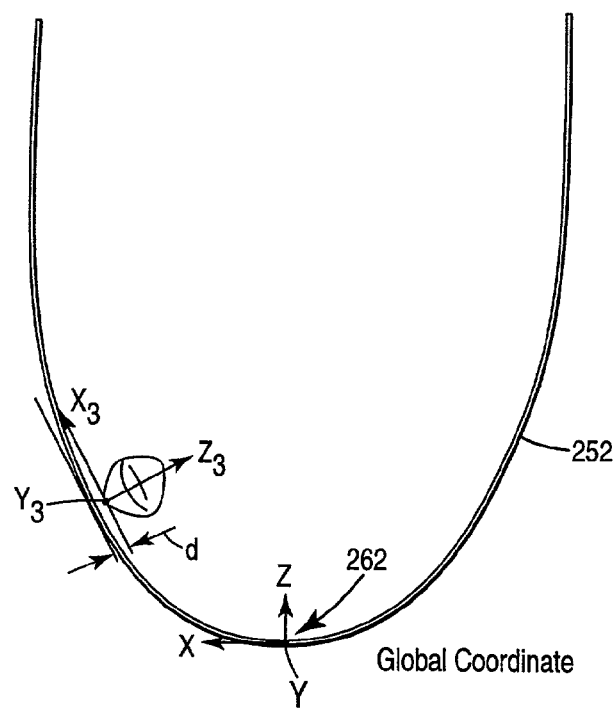

Further, as shown by block 208, and described with reference to FIG. 10D, the coordinate system $x_2$, $y_2$, $z_2$, is translated along the $z_2$ axis, or in the lingual direction, by a distance equal to the in/out value, d. This results in another local coordinate system $x_3$, $y_3$, $z_3$.

Figure 10E:
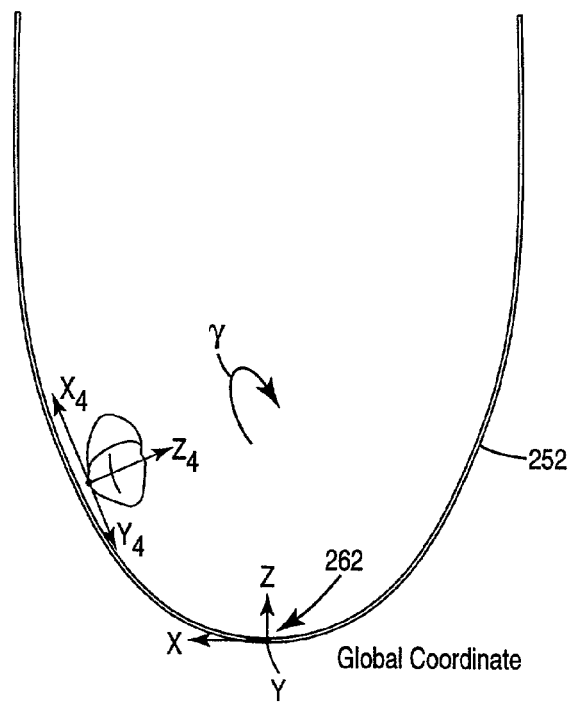

After such translation, rotation of the local coordinate system $x_3$, $y_3$, $z_3$ is performed as represented in block 210, and as shown in FIG. 10E. The coordinate system $x_3$, $y_3$, $z_3$ is rotated by an angle $\gamma$ with respect to the $z_3$ axis to the desired angulation $\gamma_a$. For lower right and upper left teeth, $\gamma=\gamma_a$, and for upper right and lower left, $\gamma=-\gamma_a$. The local coordinate system resulting from such rotation is shown in FIG. 10E as $x_4$, $y_4$, $z_4$.

Figure 10F:
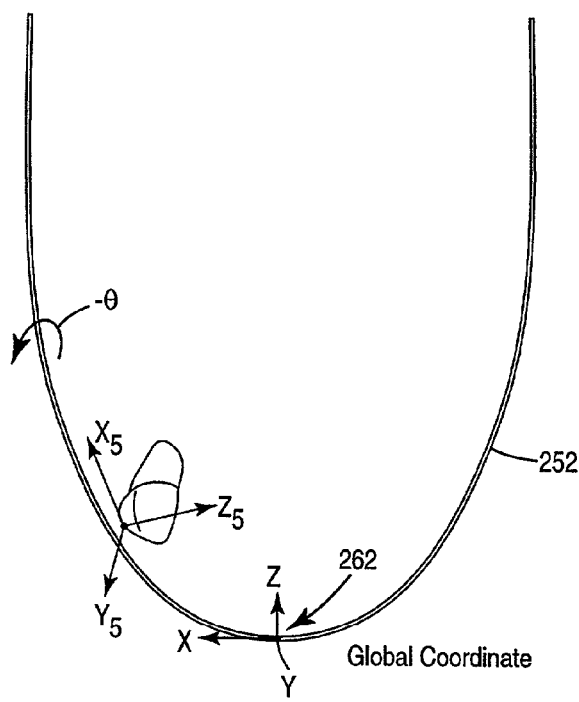

Lastly, the coordinate system $x_4$, $y_4$, $z_4$ is rotated by an angle $-\theta$ which approximates to the inclination (or torque), with respect to the $X_4$ axis to the desired inclination, $\alpha_i$, while maintaining angulation. For the lower right and upper left teeth, $\alpha=\alpha_i$, and for the upper right and lower left teeth, $\alpha=-\alpha_i$. The new coordinate system resulting from such rotation is $x_5$, $y_5$, and $z_5$, as shown in FIG. 10F.

$\theta$ is related to $\alpha$ and $\gamma$ as shown in the following equations:

$$\theta=\tan^{-1}(\tan \alpha \cos \gamma)$$

Which is derived from $$\tan(-\alpha) = -\frac{z}{y} \rightarrow y = \frac{z}{\tan\alpha}$$

$$\tan\gamma = -\frac{x}{y} \rightarrow x = -y\tan\gamma = \frac{-z\tan\gamma}{\tan\alpha}$$

$$\tan(-\theta) = -\frac{z}{\sqrt{x^2+y^2}} = \frac{-1}{\sqrt{\frac{\tan^2\gamma}{\tan^2\alpha} + \frac{1}{\tan^2\alpha}}}$$

$$= \frac{-\tan\alpha}{\sqrt{\tan^2\gamma + 1}} = -\tan\alpha\cos\gamma$$

so $$\tan\theta = \tan\alpha\cos\gamma$$

It is noted that when the angulation $\gamma$ is small, $\cos\gamma$ approaches one and $\theta$ is approximately the same as torque $\alpha$.

Thereafter, the model tooth 270 is attached to the new local coordinate system $x_5$, $y_5$, $z_5$ as shown in FIG. 10F. Although teeth are also shown in the other diagrams of FIGS. 10A–F, such teeth are provided only for illustration purposes to show rotation and translation. However, attachment of the tooth to the local coordinate system is not performed until the local coordinate system is in its proper position per the selected prescription data. By attaching the tooth after the local coordinate system has been moved, complexity of the positioning of teeth in the prescribed positions is reduced.

Attachment of the tooth 270 to the new local coordinate system $x_5$, $y_5$, $z_5$ is represented in block 214. All the teeth are moved to their particular prescribed positions as represented by block 216 until the final tooth has been placed in its prescribed position. The movement and placement process is then done (block 218).

The mathematical expression for positioning the teeth and also the brackets, as further described below, can be described as follows. Since the tooth is affixed to a local tooth coordinate system with the y-axis being tangent and parallel to the FACC (facial axis of the clinical crown as defined by Andrews), we can find the whole tooth if we locate the transformed tooth coordinate system. For instance, if we use a unit vector $u_{y5}=[0,1,0]$ on the $y_5$-axis of the tooth coordinate system, the location of the tooth relative to the global coordinate system will be as follows:

$$u_g = t_r + R_{y1}(-\beta)D^T + R_{y1}(-\beta)R_{z3}(\gamma)R_{x4}(-\theta)u_{y5}^T$$

where $D=[0,0,d]$ the in-and-out vector, $^T$ represents vector transpose and $R_{y1}(-\beta)$, $R_{z3}(-\gamma)$ and $R_{x4}(\theta)$ are the rotational transformation matrices defined as:

$$R_{y1}(-\beta) = \begin{bmatrix} \cos(-\beta) & 0 & \sin(-\beta) \\ 0 & 1 & 0 \\ -\sin(-\beta) & 0 & \cos(-\beta) \end{bmatrix} = \begin{bmatrix} \cos\beta & 0 & -\sin\beta \\ 0 & 1 & 0 \\ \sin\beta & 0 & \cos\beta \end{bmatrix}$$

-continued $$R_{z3}(\gamma) = \begin{bmatrix} \cos\gamma & -\sin\gamma & 0 \\ \sin\gamma & \cos\gamma & 0 \\ 0 & 0 & 1 \end{bmatrix}$$

$$R_{x4}(-\theta) = \begin{bmatrix} 1 & 0 & 0 \\ 0 & \cos(-\theta) & -\sin(-\theta) \\ 0 & \sin(\theta) & \cos(-\theta) \end{bmatrix} = \begin{bmatrix} 1 & 0 & 0 \\ 0 & \cos\theta & \sin\theta \\ 0 & -\sin\theta & \cos\theta \end{bmatrix}$$

We can similarly relate the $x_5$ and $z_5$ to the global coordinate system to define the location and orientation of the tooth local coordinate system. The tooth can then be attached to the tooth local coordinate system. The same procedure can be used until all the teeth are placed at the desired positions.

With further reference to FIG. 4, and the teeth positioned in the prescribed position based on the selected prescription data, the user may view such teeth on the display to determine whether the displayed teeth satisfy the user's expectations (block 176). If the user is satisfied with the displayed teeth in the prescribed position, the displayed model teeth represent the final desired positions for the teeth of the maloccluded tooth/arch model.

However, if the user is not satisfied with the teeth in the prescribed positions, then either patient information may be changed (block 174) or the prescription data may be changed (block 172). In other words, information concerning the patient may be changed such that the model teeth or the arch form are changed. Through the previous process described herein the model may be displayed to the user in a changed form. Likewise, if a prescription is changed (e.g., by selecting a new prescription for tooth positions from a database or entering various other parameters such as in/out, angulation, and torque) for one or more teeth, then the teeth are placed in the new prescribed positions and may be displayed to the user.

To assist the user in making changes to the prescription data or patient information, the user may be provided with a representation of the one or more teeth of the defined three-dimensional maloccluded tooth/arch model in desired final positions represented by the selected prescription data overlaid with a representation of the defined three-dimensional maloccluded tooth/arch model. A visual comparison can be made to assist in defining a more effective prescription. For example, simultaneous display of teeth in two or more different positions is described in U.S. patent application Ser. No. 09/918,226 filed Jul. 30, 2001 and entitled "Method and Apparatus for Selecting a Prescription for an Orthodontic Brace."

With the decision that the maloccluded model teeth are in the final desired positions, predefined and existing orthodontic brackets and/or archwires are selected from a database based on at least the maloccluded tooth/arch model and the selected prescription data corresponding to the final desired positions of the patient's teeth (block 120). Preferably, the brackets selected from the database are the brackets which best move the maloccluded teeth into the desired final positions (block 182). As previously described herein, the teeth may be moved close, but not necessarily exactly, to the desired final positions. Further, the archwire is selected by the user to attempt to best move the patient's maloccluded teeth to the desired final positions represented by the selected prescription data (block 180) at the conclusion of treatment.

For example, an archwire for the patient may be chosen from a library of predefined and existing archwires based on the arch form defined by the user (block 112) via the input of patient information. For example, the archwire may be an "Orthoform" brand archwire sold by 3M Unitek Corporation. As an example, the practitioner may select an archwire from a library of archwire data representative of parameters of predefined and existing archwires. Alternatively, or in combination with the selection and/or definition of the arch wire by the user, the system may do a database search based on the arch form information and select an archwire to be used.

Various methods of selecting the brackets (block 182) are possible. Several illustrative exemplary embodiments of bracket selection processes shall be described with reference to FIGS. 11–12.

Figure 11A:
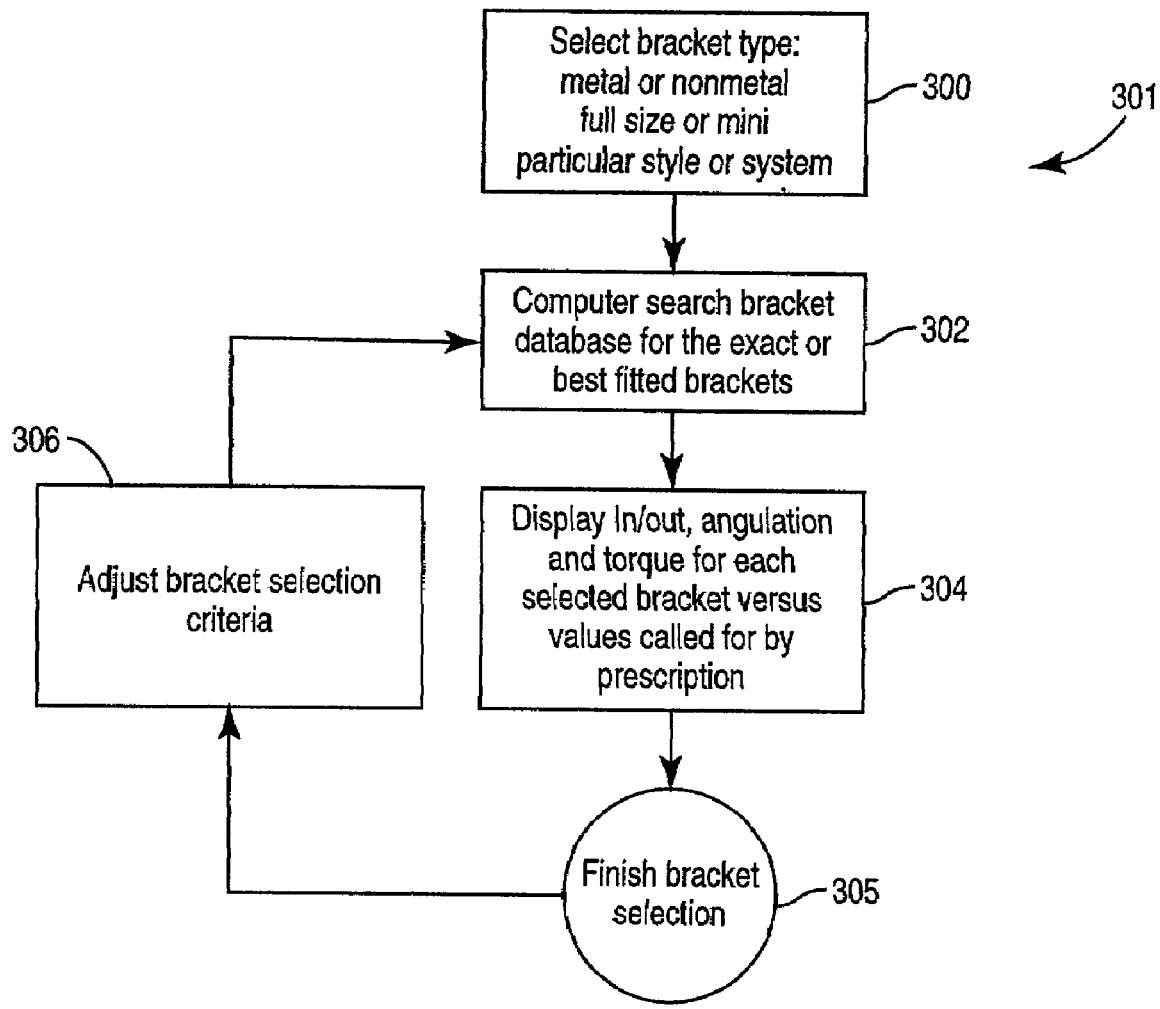
FIG. 11A is a block diagram illustrating one embodiment of the selection of predefined and existing brackets according to the selection method of FIG. 4.
Figure 11B:
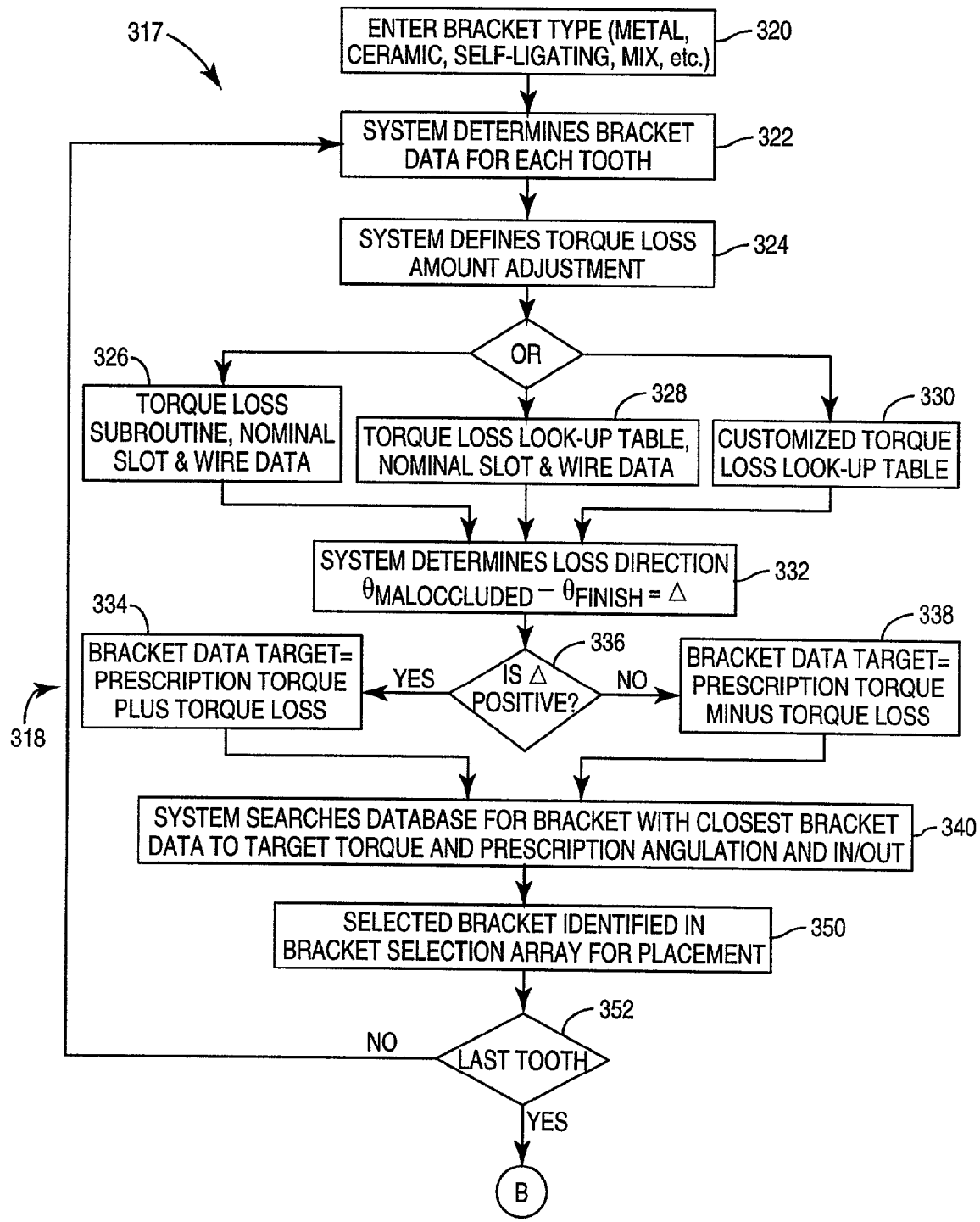
FIGS. 11B–11C (referred to herein as FIG. 11B) are another block diagram illustrating yet another embodiment of the selection of predefined and existing brackets according to the selection method of FIG. 4.
Figure 11C:
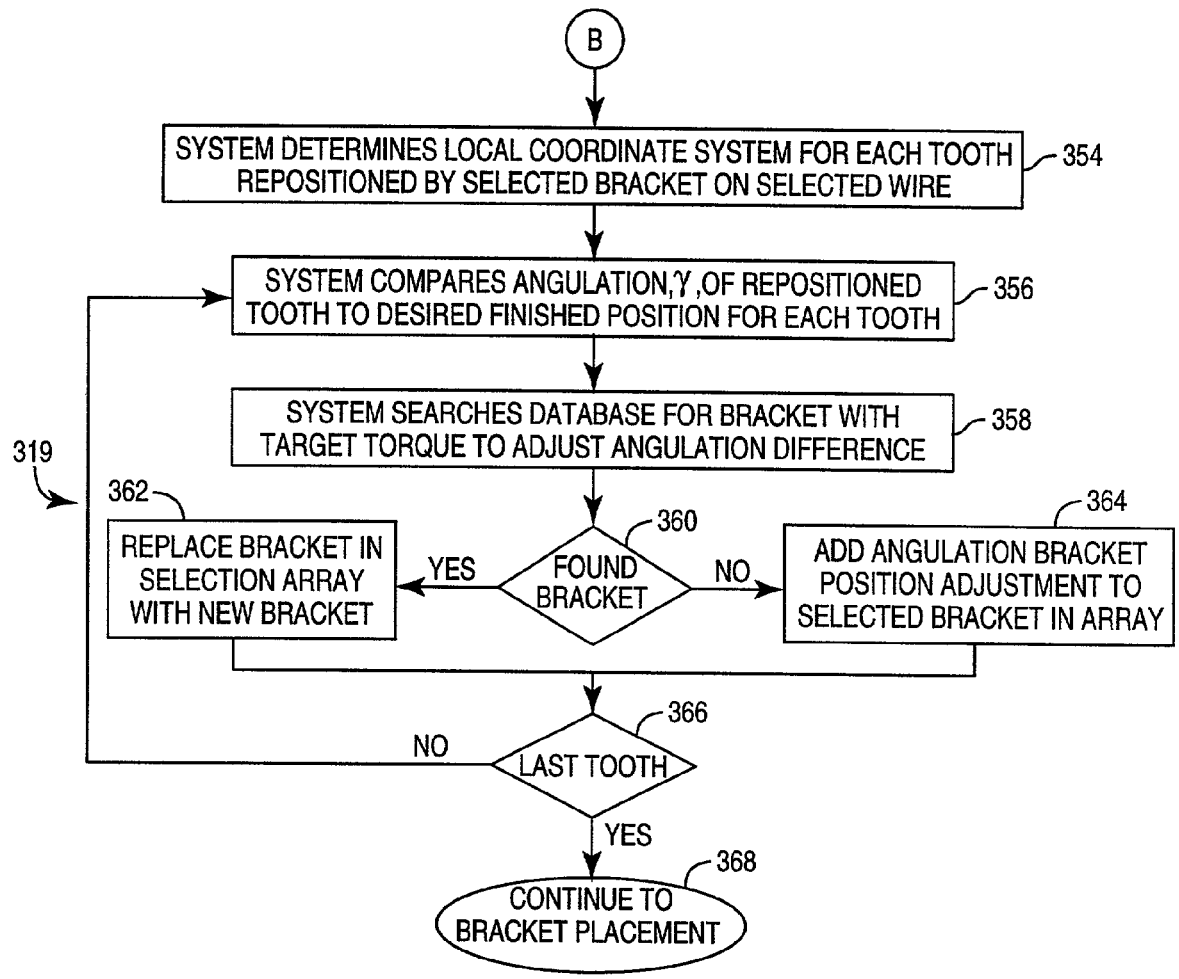

For example, a flow diagram of an illustrative bracket selection process 301 is shown in FIG. 11A. Such a process employs a database including bracket data representative of predefined and existing orthodontic brackets, such as the database 400 shown in FIG. 12 represented generally by the table 404. The database 400 includes one or more parameters defining predefined and existing brackets. For example, such parameters include torque, angulation, in/out, hook, left/right, slot size, etc. One will recognize that various other parameters may also be a part of such bracket descriptions.

With such predefined and existing brackets being defined in the database, bracket selection may proceed using a database search based substantially only on bracket selection criteria corresponding to the prescription data selected defining the desired position of teeth of the patient, e.g., torque, angulation, in/out, etc. However, preferably, a user interface is provided to allow the user to provide various types of bracket information (block 300) as shown in FIG. 11A for use in limiting the search of the database. For example, the user may be allowed to select the bracket type, e.g., metal or non-metal, fall size or miniature, a particular style or system, etc., to limit the search to some degree.

With the various bracket selection criteria provided, the computer search of the predefined and existing brackets in the database is performed to find the best orthodontic brackets that can move the maloccluded teeth to the desired final positions (block 302). For example, the best brackets may actually have a prescription that matches exactly to the final selected prescription (block 114). However, generally, as the present invention is based on estimates and only certain brackets are available for selection, as opposed to use of customized brackets, the brackets resulting from the computer search will most likely not be an exact match.

In other words, the computer search for the brackets may be performed directly from the selected prescription data (block 114) that resulted in the representation of the model teeth in the desired final positions (block 176) as shown and described with reference to FIG. 4. Such a prescription may provide bracket selection criteria 402 as shown in FIG. 12 to be used for the search of the database 400.

In addition to, or in the alternative to, using only the selected prescription data, a user interface may be provided to the user for allowing the user to modify or input bracket selection criteria based on various circumstances, such as experience, model teeth represented in the final positions (block 176), start position of teeth in the maloccluded model, or any other data, either displayed or known otherwise to the user that might affect the bracket selection process. For example, as shown in the table portion 402, the anterior lower arch bracket may have a torque greater than −5 as defined by the final desired positions of the model teeth (block 176). However, a user may wish to change such values based on prior experience.

Further, for example, the prescription data selected for the desired tooth positions may be presented to the user for confirmation prior to using such selected information for searching the database 400. This also would allow the user to have an opportunity to make bracket selection criteria changes, for example, based on experience.

Additionally, a user interface may allow the user to modify or input bracket selection criteria based on the direction of the orthodontic correction required to move a patient's maloccluded teeth to the represented final desired positions (block 176) and accommodate the clearance between the final archwire and bracket slot. In other words, the effect of the start position of the archwire in the slot of the bracket is preferably considered. Such clearance has an effect on torque loss, as well as angulation.

For example, such clearance is illustrated in FIGS. 5B'–5B" through 5D'–5D" and is preferably taken into account when selecting the brackets. For example, a tooth 500 and bracket 502 are shown in nominal positions in FIGS. 5B'–5B". The bracket 502 has a base 508 fixed to the tooth 500 with a bracket slot 506 for receiving archwire 504. Note that in the nominal positions, very little clearance between the archwire and slot exists. FIGS. 5C'–5C" show the tooth 500A starting with excess negative torque, while FIGS. 5C'–5C" show the tooth starting with excess positive torque. Using the same bracket for such varied start positions would result in completely different final positions for the different start positions. For example, as shown in FIGS. 5C'–5C", movement from tooth position 500A proceeds to 500B, while movement from tooth position 500C goes to 500D.

For start position 500A, a bracket with more positive (lingual root) torque would be selected to account for the torque loss between the bracket and the finishing archwire and yield a finished position closer to that desired. Likewise, for start position 500C, a bracket with more negative torque would be selected. As such, a user would want such characteristics to be accounted for in the bracket selection criteria prior to a search being performed. Such bracket selection criteria may be modified by the user to input more effective criteria for certain start positions of the teeth, or a computer process may automatically take into account the start positions of the maloccluded teeth to provide for a more effective bracket selection process 317 as further described below with reference to FIG. 11B.

Further, with reference to FIGS. 11A and 12, the brackets 406 selected for best moving the maloccluded to the desired final positions may be displayed with the values called for by the selected prescription (block 304) so as to provide further information to the user. In such a manner, the user may compare the selected prescription data to the bracket data, e.g., bracket prescription information, for the selected brackets and decide whether the bracket selection process should be completed (block 305) or whether adjustments in the bracket selection criteria (block 306) should be made. As shown in FIG. 12, only the resulting brackets 406 are shown for simplicity purposes.

If it is decided that the bracket selection criteria 402 needs to be adjusted (block 306), then the user is provided with an interface to modify the bracket selection criteria 402, e.g., torque, angulation, etc. Thereafter, another computer search of the bracket database is performed to find the best match brackets that correspond to the new bracket selection criteria 402 (block 302).

In one embodiment of the present invention, Microsoft Excel is utilized to provide a database of predefined and existing brackets. Using a Microsoft Excel advanced filter defined by the bracket selection criteria, an efficient bracket selection process can be performed. One skilled in the art will recognize that any database and search process may be used according to the present invention.

With further reference to FIG. 4, the predefined and existing brackets selected from the database (block 182) may be placed onto the teeth in a certain position (block 190). Data representing such brackets are stored in memory for use in placing such brackets onto the model teeth. One such bracket is illustratively shown in FIG. 9.

The brackets may be moved and placed onto the teeth in any manner as known to one skilled in the art. Preferably, substantially the same method of placing the model teeth in the prescribed positions as described with reference to process 118 of FIG. 6 is used to place the brackets onto the teeth in a prescribed position. In other words, a global coordinate system is provided on the surface of the archwire for the three-dimensional tooth/arch model. A local coordinate system is defined for the bracket, and the local coordinate system is moved relative to the global coordinate system to a position defined at least in part by the bracket prescription. Thereafter, the bracket is attached to the corresponding moved local coordinate system.

One embodiment of providing the global coordinate system is the same as described with reference to FIG. 6. In other words, the global coordinate system is initialized on the inner surface and midpoint of the archwire.

Figure 9:
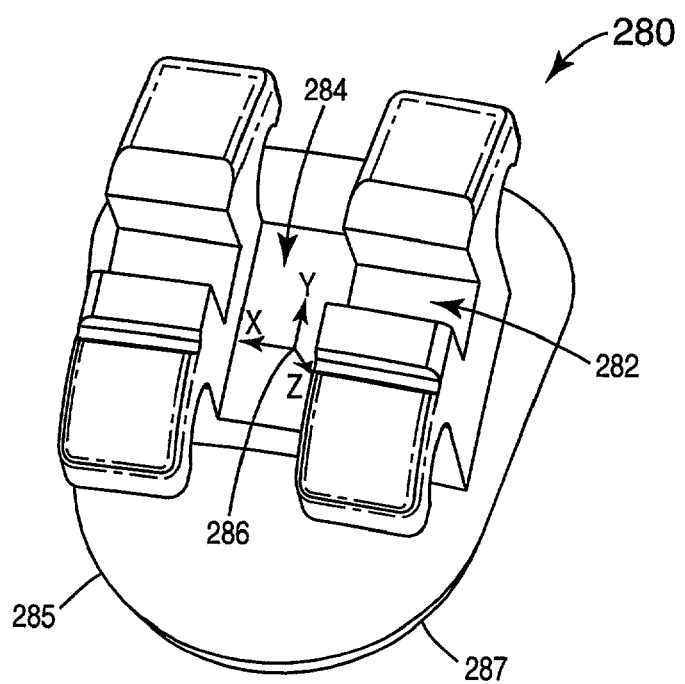
FIG. 9 shows a perspective view of a bracket having an illustrative local coordinate system defined thereon for use in a process such as described with reference to FIG. 6.

As shown in FIG. 9, the local coordinate system 284 for each bracket 280 is provided at the bottom surface 287 of the base 285 where the origin 286 of the local coordinate system 284 is at the projection of the center of the archwire slot 282 to the bracket base surface 287. The x axis of the local coordinate system 284 is in the direction of the archwire slot 282 and the y axis is tangent to the bracket base 285 in the occlusal direction. The z axis therefore is pointing in the lingual direction.

With the brackets placed on the teeth, or even prior to placing brackets on the model teeth (block 190), the teeth can be repositioned to orientations associated with the bracket data of the selected orthodontic brackets (block 192). For example, the teeth may be moved to new bracket in/out, angulation, and torque prescription values of the predefined and existing orthodontic brackets selected. One illustrative end result of the movement process is a display of the tooth model with the brackets positioned thereon.

Further, as described above, the end position of the teeth also depends on the bracket prescription interaction with the finishing archwire, particularly to compensate for the start position of the teeth. As such, selection of brackets and repositioning of the maloccluded teeth should take into account this interaction. One illustrative bracket selection process 317 that provides for such compensation shall be described with reference to FIG. 11B.

As shown in the bracket selection process 317 carried out by the system, the user enters via a user interface certain bracket information to limit the later to be performed search (block 320). For example, the information may include the bracket type, such as metal, ceramic, self-ligating, mix, etc.

The system then initializes the determination of bracket data for each tooth of the model (block 322) in a torque adjustment process 318. For example, the amount of torque loss adjustment necessary to make an effective bracket selection needs to be defined (block 324).

The amount of torque loss adjustment can be determined in any variety of ways. For example, the amount of torque loss adjustment can be determined using a subroutine (block 326) based on the nominal slot, i.e., bracket slot, and archwire data by calculating the angle at which diagonal corners of the archwire would contact the occlusal and gingival walls of the bracket slot using an average wire corner radius.

Further, for example, the amount of torque loss adjustment can be determined with use of a look up table based on nominal slot and archwire data. In other words, a certain amount of torque loss adjustment is selected using the look up table based on selecting the contact angle from an array of values pre-calculated using standard slot, archwire and corner radius data.

Yet further, the amount of torque loss adjustment can be determined with use of a customized torque loss look up table including amounts of torque loss that can be looked up based on selecting the contact angle from an array of values modified by or for the user through a user interface. Custom correction angles would be pre-calculated and entered into the table based on special wire and slot combinations or developed as the result of the user's own clinical experience.

After determination of the amount of torque loss adjustment (block 332), the direction that the loss occurs must be determined (block 332) such that the proper direction adjustment can be made to the prescription data, e.g., torque data. Such direction of loss may be determine by $\theta_{MALOCCLUDED} - \theta_{FINISH} = \Delta$, where $\theta$ is the adjusted torque angle applied to the local coordinate system and $\Delta$ is the difference between the adjusted torque in the maloccluded tooth local coordinate system, and the adjusted torque in the finished position local coordinate system for that tooth.

If $\Delta$ is positive per decision block 336, then the desired or adjusted target bracket data to account for torque loss (i.e., bracket selection criteria for torque) is equal to the torque of the selected prescription data plus the determined amount of torque loss adjustment. Likewise, if $\Delta$ is negative per decision block 336, then the desired or adjusted target bracket data to account for torque loss (i.e., bracket selection criteria for torque) is equal to the torque of the selected prescription data minus the determined amount of torque loss adjustment.

With the torque adjustment taken into consideration, the system can then search the database for brackets with the closest bracket data to the target adjusted torque bracket selection criteria along with angulation and in/out as defined by the selected prescription data (block 340). In other words, at least in one embodiment, the bracket selection criteria used for the search are the torque of the prescription data adjusted for torque loss due to the slot/archwire interaction, along with angulation and in/out from the prescription data (e.g., selected prescription data per block 114).

After selection of a bracket per the torque adjustment process 318, the bracket identified from the predefined and existing brackets in the database is then ready for placement on the tooth (block 350) with the other brackets of the selected array of brackets for the teeth. The process is repeated for each of the teeth until brackets have been selected for each tooth (block 352).

Once brackets have been selected based on an adjusted torque, then the teeth are repositioned based on the bracket data for the selected brackets as previously described herein (block 354). In other words, the local coordinate system for each tooth (i.e., each tooth being repositioned based on the bracket data for the selected bracket on the selected archwire) is determined. The teeth may then be attached to the local coordinate system.

With the teeth repositioned based on the bracket selection made using the adjustment for torque loss, an angulation adjustment process 319 is then preferably employed. The adjustment process 319 may be provided, on a tooth by tooth basis, by first comparing the angulation, γ, of the tooth to the desired finished position for the tooth as defined by the selected prescription (block 356).

Using the angulation difference, the bracket search criteria can be modified with an adjusted target torque that also adjusts for the angulation difference so that the tooth can be moved closer to the desired finished position as defined by the selected prescription. A search of the database for a new bracket using the target torque and the other previously defined criteria, e.g., in/out, is then performed (block 358).

If a bracket is found that matches the adjusted target torque and adjusted angulation (or is within a certain deviation therefrom), according to decision block 360, the new bracket selected replaces the previously selected bracket in the selection array of brackets for the teeth (block 362). However, if a bracket is not found that matches the adjusted target torque (or is within a certain deviation therefrom), according to decision block 360, the position of the bracket on the tooth is adjusted to compensate for the angulation difference (block 364).

The angulation adjustment process 319 continues for each of the teeth as represented by block 366 and the loop back to block 356. Once angulation adjustment is performed for all of the teeth, bracket placement is performed (block 368) along with repositioning of the teeth according to the final brackets selected. For example, position of the bracket on the tooth is performed according to the bracket data as adjusted taking into consideration angulation difference as just described.

It will be recognized that the above torque and angulation processes are only illustrative exemplary embodiments for carrying out adjustments for the selection of brackets based on the interaction of the archwire with the slot of the brackets, e.g., such interaction due to at least in part the starting position of teeth, the size of the slots, the size and shape of the archwire, etc., and in no manner are such processes the only way to make such adjustments. At least a portion of the novelty of the present invention is the recognition and implementation of a method to select predefined and existing brackets while taking into consideration such interaction between the archwire and slot of the brackets. Such processes may be implemented in an automated bracket selection process alone or in combination with information or adjustments provided through a user interface.

Also, variations in bracket fit to the teeth could be accommodated during bracket bonding by use of indirect bonding, where brackets are first bonded to a physical model of the patient's teeth and transferred to the patient using a placement tray or the like. Computer controlled placement of the bracket during either direct or indirect bonding could maintain the selected prescription.

With further reference to FIG. 4, and with the teeth repositioned based on the bracket data, a bracket selection adjustment process 122 may then be employed to attempt to provide for selection of even more effective orthodontic brackets. In the adjustment process, for example, with the teeth of the maloccluded model placed in the positions based on the bracket data, e.g., bracket data and interaction with the archwire, the user may view such teeth on the display to determine whether the displayed repositioned teeth satisfy the user's expectations, e.g., match the final desired positions for the teeth. If the user is satisfied with the displayed repositioned teeth, then the user can move forward and the final teeth/bracket model representation with the final bracket selection can be provided (block 126).

However, if the user is not satisfied with the teeth position in the tooth/arch model based on selected brackets, then the bracket selection can be changed (block 124). For example, different bracket selection criteria may be used to change the bracket selection. In other words, information concerning the process of selecting brackets may be changed such that a new selection of brackets is provided. The teeth of the maloccluded model may then be represented based on the new selection of brackets and through the previous process described herein displayed to the user in a changed form. This process can be reiterated until the user is satisfied with the resultant teeth repositioned based on the newly selected brackets.

To assist the user in making changes to the brackets selected, the user may be provided with a representation of the one or more teeth of the defined three-dimensional maloccluded tooth/arch model in desired final positions represented by the selected prescription data overlaid with a representation of the one or more teeth of the defined three-dimensional maloccluded tooth/arch model as repositioned based on the bracket data representative of the selected brackets (block 194). Such a comparison can be used by a user to modify the bracket selection.

Further, to help view the tooth model with the brackets, the user of the system can use a mouse or other pointing device to identify and drag a certain tooth, teeth and/or bracket(s) for translation or rotation. The computer can update the display to the new positions in real time. The user or patient can view the tooth model with or without the brackets from different viewing points and angles. Multimedia presentations such as sound to represent collision between two teeth or brackets, or between teeth and brackets, can also be provided.

After a final selection of brackets is made, the repositioned model corresponding to the final bracket selection may be displayed (block 126).

Further, upon selection of the brackets using the method of the present invention, the user may apply brackets to the patient's teeth. Such brackets may be brackets precoated with an adhesive material, e.g., at the manufacturer or in an orthodontist's office.

One illustrative embodiment of the use of the bracket selection method of the present invention shall be described below. It will be recognized that the various techniques described previously herein and below may be used together or certain techniques can be used alone to assist in bracket selection.

According to the illustrative method of use by an orthodontic user, the user would maintain an in-office inventory of predefined and existing brackets. To maintain a minimum practical number of brackets, this inventory would include the most popular bracket types in the user's preferred prescription, plus brackets with feature options, such as with or without hooks, and prescription options, such as additional torques and angulations. These additional brackets could be limited to those most commonly used based on patient statistics. The inventory provides a ready supply of brackets for initial patient bonding as well as replacement brackets when required. As the selection system uses brackets, a running count could be kept to maintain the in-office inventory.

For bracket selection, the orthodontic user would enter patient information via a user interface into a computer using the bracket selection program previously described herein. A maloccluded model for the patient may be defined through an iterative process described previously herein. The system would use the information in its tooth/arch model database to produce a virtual maloccluded tooth/arch model to closely represent the patient's teeth and arch. The generated maloccluded tooth/arch model may then be displayed to the user for modification if desired through a user interface.

The user would then select an initial prescription for the patient, and through an iterative process as previously described herein, the one or more teeth of the maloccluded model for the patient may be moved to the desired final positions as prescribed. Through an iterative process described previously herein the system would use the prescription selected to provide a tooth/arch model having the teeth in the prescribed occlusion. The generated tooth/arch model with the teeth in the prescribed positions may be displayed to the user for modification if desired through a user interface, e.g., entry of new or modified patient information or new or modified prescription information.

When the user is satisfied with the final desired tooth positions for the teeth, the system continues with selection of brackets from a database of existing and predefined orthodontic brackets that best move the maloccluded teeth to the desired prescribed positions. Through the input of additional bracket criteria, if required, using the processes described previously herein (e.g., selection using torque adjustment), the system selects the specific brackets, places and displays bracket representations thereof on the tooth/arch model. Through an iterative process of displaying the teeth based on bracket data associated with the selected brackets and then modifying the bracket selection, if desired (e.g., based on a comparison to the desired positions based on the prescription selected) the system would generate a final tooth/arch model with the teeth in the final positions based on a final bracket selection.

After the user makes the final adjustments and the final brackets are selected, the bracket selection process is complete. The chosen brackets would be dispensed from the in-office inventory for application at time of the actual bonding procedure. If, in an exceptional case, the selected bracket is not in the inventory, it could be procured from a supplier prior to the time of bonding the set of brackets. Beyond the selection process, the information in the system could be utilized to guide the placement of the bonded brackets for the specific patient by direct or indirect bonding methods.

All patents, patent documents (including applications), and publications cited herein are incorporated by reference as if each were individually incorporated by reference. Various modifications of this invention will be apparent to those skilled in the art without departing from the scope of this invention, and it should be understood that this invention is not limited to the illustrative embodiments set forth herein. For example, various databases may be used to provide the information, various manipulation graphical software packages may be used to provide for manipulation of images, various types of software programming may implement the general functionality described herein, etc.

What is claimed is:

1. A computer-implemented method of orthodontic appliance selection, the method comprising:
   providing tooth/arch model data;
   defining a three-dimensional maloccluded tooth/arch model using the tooth/arch model data as a function of patient information;
   presenting a user interface to receive from a user prescription data representative of user-specified desired final positions for one or more teeth of the defined three-dimensional maloccluded tooth/arch model;
   providing bracket data representative of one or more parameters defining a plurality of predefined and existing orthodontic brackets;
   executing bracket selection software to select one or more of the plurality of predefined and existing orthodontic brackets for use in moving one or more teeth of the defined three-dimensional maloccluded tooth/arch model to the user-specified desired final positions based on at least the prescription data; and displaying the selected one or more predefined and existing orthodontic brackets.

2. The method of claim 1,
   wherein selecting one or more of the plurality of predefined and existing orthodontic brackets comprises selecting one or more of the plurality of predefined and existing orthodontic brackets that move the one or more teeth of the defined three-dimensional maloccluded tooth/arch model at least close to, but not necessarily exactly to, the desired final positions represented by the prescription data; and
   wherein the method further comprises repositioning the one or more teeth of the defined three-dimensional maloccluded tooth/arch model to positions based on at least bracket data representative of the selected predefined and existing orthodontic brackets.

3. The method of claim 2, wherein the method further comprises displaying the repositioned one or more teeth of the defined three-dimensional maloccluded tooth/arch model with the selected predefined and existing orthodontic brackets.

4. The method of claim 2, wherein the method further comprises:
   providing a representation of the one or more teeth of the defined three-dimensional maloccluded tooth/arch model in desired final positions represented by the prescription data; and
   providing a representation of the one or more teeth of the defined three-dimensional maloccluded tooth/arch model as repositioned for use in comparison to the representation of the one or more teeth of the defined three-dimensional maloccluded tooth/arch model in desired final positions represented by the prescription data.

5. The method of claim 4, wherein the method further comprises receiving input from the user modifying the selection of the one or more of the plurality of predefined and existing orthodontic brackets for use in moving one or more teeth of the defined three-dimensional maloccluded tooth/arch model to the desired final positions based on the comparison.

6. The method of claim 1, wherein the method further comprises:
   providing archwire data representative of one or more parameters defining a plurality of predefined and existing orthodontic archwires; and
   selecting at least one of the plurality of predefined and existing orthodontic archwires for use in moving the one or more teeth of the defined three-dimensional maloccluded tooth/arch model to the desired final positions.

7. The method of claim 6,
   wherein selecting one or more of the plurality of predefined and existing orthodontic brackets comprises selecting one or more of the plurality of predefined and existing orthodontic brackets that move the one or more teeth of the defined three-dimensional maloccluded tooth/arch model at least close to, but not necessarily exactly to, the desired final positions represented by the prescription data; and wherein the method further comprises repositioning the one or more teeth of the defined three-dimensional maloccluded tooth/arch model to positions based on at least bracket data representative of the selected one or more predefined and existing orthodontic brackets and archwire data representative of the selected at least one predefined and existing orthodontic archwire.

8. The method of claim 7, wherein the method further comprises displaying the repositioned one or more teeth of the defined three-dimensional maloccluded tooth/arch model with the selected one or more predefined and existing orthodontic brackets interacting with the selected at least one predefined and existing orthodontic archwire.

9. The method of claim 7, wherein the method further comprises:
   providing a representation of the one or more teeth of the defined three-dimensional maloccluded tooth/arch model in desired final positions represented by the prescription data; and
   providing a representation of the one or more teeth of the defined three-dimensional maloccluded tooth/arch model as repositioned for use in comparison to the representation of the one or more teeth of the defined three-dimensional maloccluded tooth/arch model in desired final positions represented by the prescription data.

10. The method of claim 9, wherein the method further comprises modifying at least the selection of the one or more of the plurality of predefined and existing orthodontic brackets for use in moving one or more teeth of the defined three-dimensional maloccluded tooth/arch model to the desired final positions based on the comparison.

11. The method of claim 10, wherein the method further comprises:
   repeatedly providing a representation of the one or more teeth of the defined three-dimensional maloccluded tooth/arch model as repositioned based on the bracket data representative of multiple modified selections of one or more orthodontic brackets for use in comparison to the representation of the one or more teeth of the defined three-dimensional maloccluded tooth/arch model in desired final positions represented by the prescription data; and
   modifying, after each comparison, at least the selection of the one or more of the plurality of predefined and existing orthodontic brackets for use in moving one or more teeth of the defined three-dimensional maloccluded tooth/arch model to the desired final positions.

12. The method of claim 1, wherein defining the three-dimensional maloccluded tooth/arch model using the model data as a function of patient information comprises providing a user input interface to a user to allow input of one or more characteristics associated with a patient.

13. The method of claim 12, wherein the one or more characteristics comprise at least one of gender, age, race, tooth size, arch size, impression information, and arch shape.

14. The method of claim 1, wherein the one or more teeth of the defined three-dimensional maloccluded tooth/arch model comprise individual separated three-dimensional models of teeth.

15. The method of claim 1, wherein the method further comprises:
   providing a representation of one or more teeth of the defined three-dimensional maloccluded tooth/arch model for a patient;
   providing one or more patient images representative of the patient's actual teeth for use in comparison to the representation of the one or more teeth of the defined three-dimensional maloccluded tooth/arch model; and
   modifying the defined three-dimensional maloccluded tooth/arch model based on the comparison.

16. The method of claim 15, wherein the one or more patient images comprise at least one of two-dimensional images and three-dimensional images of one or more portions of the patient's teeth.

17. The method of claim 1, wherein the method further comprises:
   providing a representation of the one or more teeth of the defined three-dimensional maloccluded tooth/arch model for a patient; and
   providing a representation of the one or more teeth of the defined three-dimensional maloccluded tooth/arch model in desired final positions represented by the prescription data.

18. The method of claim 17, wherein the method further comprises changing patient information or prescription data resulting in a modification to the representation of one or more teeth of the defined three-dimensional maloccluded tooth/arch model or the representation of the one or more teeth of the defined three-dimensional maloccluded tooth/arch model in desired final positions represented by the prescription data.

19. The method of claim 1, wherein the method further comprises providing a representation of the one or more teeth of the defined three-dimensional maloccluded tooth/arch model for a patient in desired final positions represented by the prescription data, wherein providing the representation comprises:
   providing a global coordinate system on a surface of at least one archwire of the three-dimensional tooth/arch model, the archwire corresponding to an arch form of the patient;
   defining a local coordinate system at a facial axis point of each tooth of the three-dimensional tooth/arch model;
   placing the local coordinate system corresponding to each tooth relative to the global coordinate system to a position in the three-dimensional tooth/arch model based at least in part on the prescription data; and
   attaching each tooth to the corresponding placed local coordinate system.

20. The method of claim 19, wherein the method further comprises repositioning the one or more teeth of the defined three-dimensional maloccluded tooth/arch model to positions based on at least bracket data representative of the selected predefined and existing orthodontic brackets, wherein the repositioning of the one or more teeth of the defined three-dimensional maloccluded tooth/arch model in positions based on at least bracket data comprises changing the placement of the local coordinate system relative to the global coordinate system for each tooth and attaching each tooth to the new placement of the local coordinate system.

21. The method of claim 19, wherein the method further comprises repositioning the one or more teeth of the defined three-dimensional maloccluded tooth/arch model to positions based on at least bracket data representative of the selected predefined and existing orthodontic brackets, wherein the repositioning of the one or more teeth of the defined three-dimensional maloccluded tooth/arch model in positions based on at least bracket data comprises:

providing a global coordinate system on a surface of at least one archwire of the three-dimensional tooth/arch model, the archwire corresponding to an arch form of the patient;

defining a local coordinate system at a facial axis point of each tooth of the three-dimensional tooth/arch model;

placing the local coordinate system corresponding to each tooth relative to the global coordinate system to a position defined at least in part by at least the bracket data representative of the selected one or more predefined orthodontic brackets; and attaching each tooth to the corresponding placed local coordinate system.

22. The method of claim 19, wherein the local coordinate system for each tooth initially coincides with the global coordinate system (xyz), where x is in the direction of the archwire, y is in the occlusal direction, and z is in the lingual direction, wherein placing the local coordinate system corresponding to each tooth to a position defined at least in part by at least the prescription data comprises:

translating the local coordinate system of each tooth, relative to the global coordinate system, along the archwire based on tooth type to provide a first local coordinate system, the first local coordinate system comprising $x_1 y_1 z_1$;

rotating the first local coordinate system of each tooth such that $z_1$ is perpendicular to an inner surface of the archwire to provide a second local coordinate system $x_2 y_2 z_2$;

translating the second local coordinate system in the lingual direction by a distance along $z_2$ corresponding to the in/out of the prescription data to provide a third local coordinate system $x_3 y_3 z_3$;

rotating the third local coordinate system by an angle with respect to $z_3$ corresponding to angulation of the prescription data to provide a fourth local coordinate system $x_4 y_4 z_4$; and rotating the fourth local coordinate system by an angle with respect to $x_4$ corresponding to a torque of the prescription data to provide a fifth local coordinate system $x_5 y_5 z_5$.

23. The method of claim 19, wherein the method further comprises:

providing archwire data representative of one or more parameters defining a plurality of predefined and existing orthodontic archwires;

selecting at least one of the plurality of predefined and existing archwires for use in moving the one or more teeth of the defined three-dimensional maloccluded tooth/arch model to the desired final positions; and repositioning the one or more teeth of the defined three-dimensional maloccluded tooth/arch model to positions based on at least bracket data representative of the selected one or more predefined and existing orthodontic brackets and archwire data representative of the selected at least one predefined and existing orthodontic archwire.

24. The method of claim 21, wherein the method further comprises repositioning the one or more teeth of the defined three-dimensional maloccluded tooth/arch model to positions based on at least bracket data representative of the selected predefined and existing orthodontic brackets, wherein the repositioning of the one or more teeth of the defined three-dimensional maloccluded tooth/arch model in positions based on at least bracket data comprises providing a representation of at least teeth of the selected three-dimensional tooth/arch model in positions defined by the selected prescription along with the selected predefined and existing orthodontic brackets.

25. The method of claim 24, wherein providing the representation of the selected predefined and existing orthodontic brackets comprises:

providing a global coordinate system on a surface of an archwire of the three-dimensional tooth/arch model;

defining a local coordinate system having an origin located on a bottom surface of a base relative to an archwire slot center of each selected predefined and existing orthodontic bracket;

placing the local coordinate system corresponding to each of the selected predefined and existing orthodontic brackets relative to the global coordinate system to a position defined at least in part by the bracket data; and attaching each bracket to the corresponding placed local coordinate system.

26. The method of claim 1, wherein selecting one or more of the plurality of predefined and existing orthodontic brackets based on at least the prescription data comprises providing a user input interface to a user allowing the user to provide or modify one or more prescription bracket selection criteria, wherein the one or more prescription bracket selection criteria comprise at least one of torque, angulation, and in/out value.

27. The method of claim 1, wherein selecting one or more of the plurality of predefined and existing orthodontic brackets based on at least the prescription data comprises selecting one or more of the plurality of predefined and existing orthodontic brackets based on at least the prescription data and also based on an adjustment to at least one of torque or angulation due to the interaction of an archwire with slots of selected brackets.

28. The method of claim 1, wherein selecting one or more of the plurality of predefined and existing orthodontic brackets comprises selecting one or more of the plurality of predefined and existing orthodontic brackets from a database using one or mare prescription bracket selection criteria, wherein the one or more prescription bracket selection criteria comprise at least one of torque, angulation, and in/out value.

29. A computer readable medium tangibly embodying a program executable for use in selection of orthodontic appliances, wherein the computer readable medium comprises:

means for recognizing tooth/arch model data for use in defining a three-dimensional maloccluded tooth/arch model;

user interface means for allowing a user to define a three-dimensional maloccluded tooth/arch model as a function of patient information;

user interface means for allowing a user to define prescription data representative of desired final tooth positions for one or more teeth of the defined three-dimensional maloccluded tooth/arch model;

means for recognizing bracket data representative of one or more parameters defining a plurality of predefined and existing orthodontic brackets;

means for causing the display of a representation of the desired final toot positions for one or more teeth of the defined three-dimensional maloccluded tooth/arch model based on the prescription data;

means for executing a computer-implemented bracket selection process to select of one or more of a plurality of predefined and existing orthodontic brackets that move the one or more teeth of the defined three-dimensional maloccluded tooth/arch model at least close to, but not necessarily exactly to, the user-defined desired final positions represented by the prescription data;

means for causing the display of the selection of the one or more of the plurality of orthodontic brackets; and means for causing the display of a representation of one or more teeth of the defined three-dimensional maloccluded tooth/arch model in positions based on bracket data representative of the selected one or more of the plurality of predefined and existing orthodontic brackets.

30. The medium of claim 29, wherein the patient information comprises at least one of gender, age, race, tooth size, arch size, impression information, and arch shape.

31. The medium of claim 29, wherein the means for causing the display of a representation of the desired final tooth positions for one or more teeth of the defined three-dimensional maloccluded tooth/arch model based on the prescription data comprises:
   means for providing a global coordinate system on a surface of an archwire of the three-dimensional tooth/arch model;
   means for defining a local coordinate system at a facial axis point of each tooth of the three-dimensional tooth/arch model;
   means for placing the local coordinate system corresponding to each tooth relative to the global coordinate system to a position defined at least in part by the prescription data; and
   means for attaching each tooth to the corresponding moved local coordinate system.

32. The medium of claim 29, wherein the computer readable medium further comprises:
   means for causing display of one or more teeth of the defined three-dimensional maloccluded tooth/arch model for a patient; and
   means for causing the display of one or more patient images representative of the patient's actual teeth for use in comparison to the representation of the one or more teeth of the defined three-dimensional maloccluded tooth/arch model.

33. The method of claim 29, wherein the one or more teeth of the defined three-dimensional maloccluded tooth/arch model comprise individual separated three-dimensional models of teeth.

34. The medium of claim 29, wherein the computer readable medium further comprises means for causing the display of the representation of the selected predefined and existing orthodontic brackets, wherein the means for causing the display of the representation of the selected predefined and existing orthodontic brackets comprises:
   means for providing a global coordinate system on a surface of an archwire of the three-dimensional tooth/arch model;
   means for defining a local coordinate system having an origin located on a bottom surface of a base at a point relative to an archwire slot center of each selected predefined and existing orthodontic bracket;
   means for placing the local coordinate system corresponding to each of the selected predefined and existing orthodontic brackets relative to the global coordinate system to a position defined at least in part by the bracket data representative of the selected predefined and existing orthodontic brackets; and
   means for attaching each bracket to the corresponding moved local coordinate system.

35. A method of orthodontic appliance selection, the method comprising:
   providing tooth/arch model data for use in defining a three-dimensional maloccluded tooth/arch model;
   providing a user interface for allowing a user to define a three-dimensional maloccluded tooth/arch model as a function of patient information;
   providing a user interface for allowing a user to define prescription data representative of desired final tooth positions for one or more teeth of the defined three-dimensional maloccluded tooth/arch model;
   providing bracket data representative of one or more parameters defining a plurality of predefined and existing orthodontic brackets;
   executing bracket selection software to select one or more of the plurality of predefined and existing orthodontic brackets from a database for use in moving one or more teeth of the defined three-dimensional maloccluded tooth/arch model to the desired final positions based on at least the prescription data;
   displaying a representation of the desired final tooth positions for one or more teeth of the defined three-dimensional maloccluded tooth/arch model based on the prescription data;
   displaying a representation of one or more teeth of the defined three-dimensional maloccluded tooth/arch model in positions based on bracket data representative of the selected predefined and existing orthodontic brackets;
   overlaying the representation of the desired final tooth positions for one or more teeth of the defined three-dimensional maloccluded tooth/arch model and the representation of one or more teeth of the defined three-dimensional maloccluded tooth/arch model in positions based on bracket data; and
   modifying the selection of one or more of the plurality of predefined and existing orthodontic brackets from a database based on the overlaid representations.

36. The method of claim 35, wherein the method further comprises allowing the user to modify at least one of the displayed representations by selecting and dragging one of a bracket or tooth to a position.

37. The method of claim 35, wherein the method further comprises providing sound representative of contact between teeth, between one or more teeth and one or more brackets, and/or between brackets.

38. The method of claim 35, wherein the method further comprises providing a representation of selected predefined and existing orthodontic brackets with the representation of the one or more teeth in positions based on bracket data representative of the selected predefined and existing orthodontic brackets.

39. The method of claim 35, wherein selecting the three-dimensional maloccluded tooth/arch model as a function of patient information comprises providing a user input interface to the user allowing the user to input one or more characteristics associated with a patient.

40. The method of claim 39, wherein the one or more characteristics comprises at least one of gender, age, race, tooth size, arch size, impression information, and arch shape.

41. The method of claim 35, wherein the method further comprises:
   providing one or more patient images representative of the actual teeth of the patient for use in comparison to the representation of the one or more teeth of the defined three-dimensional maloccluded tooth/arch model; and modifying the defined three-dimensional maloccluded tooth/arch model based on the comparison.

42. The method of claim 41, wherein the one or more patient images comprise at least one of two-dimensional images and three-dimensional images of one or more portions of the patient's teeth.

43. The method of claim 35, wherein the method further comprises:

providing a representation of one or more teeth of the defined three-dimensional maloccluded tooth/arch model;

providing a representation of the one or more teeth of the defined three-dimensional maloccluded tooth/arch model in desired final positions represented by the prescription data; and changing patient information or prescription data resulting in a modification to the representation of one or more teeth of the defined three-dimensional maloccluded tooth/arch model or the representation of the one or more teeth of the defined three-dimensional maloccluded tooth/arch model in desired final positions represented by the prescription data.

44. A method of orthodontic appliance selection, the method comprising:

providing tooth/arch model data representative of at least one or more teeth;

defining a three-dimensional maloccluded tooth/arch model using the tooth/arch model data as a function of patient information;

providing prescription data representative of user-specified desired final positions for one or more teeth of the defined maloccluded tooth/arch model;

providing archwire data representative of one or more parameters defining a plurality of predefined and existing orthodontic archwires;

selecting at least one of the plurality of predefined and existing archwires for use in moving one or more teeth of the defined three-dimensional maloccluded tooth/arch model to the desired final positions;

providing bracket data representative of one or more parameters defining a plurality of predefined and existing orthodontic brackets;

executing bracket selection software to select one or more of the plurality of predefined and existing orthodontic brackets for use in moving one or more teeth of the defined three-dimensional maloccluded tooth/arch model to the desired final positions based on at least the prescription data; and displaying the selected one or more predefined and existing orthodontic brackets.

45. The method of claim 44, wherein selecting one or more of the plurality of predefined and existing orthodontic brackets comprises selecting one or more of the plurality of predefined and existing orthodontic brackets that move the one or more teeth of the defined three-dimensional maloccluded tooth/arch model at least close to, but not necessarily exactly to, the desired final positions represented by the prescription data; and wherein the method further comprises repositioning the one or more teeth of the defined three-dimensional maloccluded tooth/arch model in positions based on at least bracket data representative of the selected one or more predefined and existing orthodontic brackets and archwire data representative of the selected at least one predefined and existing orthodontic archwires.

46. The method of claim 45, wherein the method further comprises displaying the repositioned one or more teeth of the defined three-dimensional maloccluded tooth/arch model to the desired final positions based on at least bracket data representative of the selected one or more predefined and existing orthodontic brackets interacting with the selected at least one predefined and existing orthodontic archwires.

47. The method of claim 44, wherein the method further comprises:

providing a representation of the one or more teeth of the defined three-dimensional maloccluded tooth/arch model in desired final positions represented by the prescription data; and providing a representation of the one or more teeth of the defined three-dimensional maloccluded tooth/arch model as repositioned based on at least the bracket data and the archwire data for use in comparison to the representation of the one or more teeth of the defined three-dimensional maloccluded tooth/arch model in desired final positions.

48. The method of claim 47, wherein the method further comprises modifying at least the selection of the one or more of the plurality of predefined and existing orthodontic brackets for use in moving one or more teeth of the defined three-dimensional maloccluded tooth/arch model to the desired final positions based on the comparison.

49. The method of claim 44, wherein defining a three-dimensional maloccluded tooth/arch model using the model data as a function of patient information comprises providing a user input interface to a user allowing the user to input one or more characteristics associated with a patient.

50. The method of claim 49, wherein the one or more characteristics comprises at least one of gender, age, race, tooth size, arch size, impression information, and arch shape.

51. The method of claim 44, wherein the one or more teeth of the defined three-dimensional maloccluded tooth/arch model comprise individual separated three-dimensional models of teeth.

52. The method of claim 44, wherein selecting one or more of the plurality of predefined and existing orthodontic brackets based on at least the defined three-dimensional maloccluded tooth/arch model and the defined prescription data comprises providing a user input interface to a user allowing the user to provide or modify one or more prescription bracket selection criteria, wherein the one or more prescription bracket selection criteria comprise at least one of torque, angulation, and in/out value.

53. The method of claim 44, wherein selecting one or more of the plurality of predefined and existing orthodontic brackets comprises selecting one or more of the plurality of predefined and existing orthodontic brackets based on at least the prescription data and also based on an adjustment to at least one of torque or angulation due to the interaction of an archwire with slots of selected brackets.

54. The method of claim 44, wherein selecting one or more of the plurality of predefined and existing orthodontic brackets comprises selecting one or more of the plurality of predefined and existing orthodontic brackets from the database using one or more prescription bracket selection criteria, wherein the one or more prescription bracket selection criteria comprise at least one of torque, angulation, and in/out value.

55. The method of claim 44, wherein the plurality of predefined and existing orthodontic brackets comprises a plurality of predefined and existing orthodontic brackets precoated with a precoat adhesive material.

56. The method of claim 44, wherein the method further comprises:
   providing a representation of one or more teeth of the defined three-dimensional maloccluded tooth/arch model for a patient;
   providing one or more patient images representative of actual teeth of the patient for use in comparison to the representation of the one or more teeth of the defined three-dimensional maloccluded tooth/arch model; and
   modifying the defined three-dimensional maloccluded tooth/arch model based on the comparison.

57. The method of claim 56, wherein the one or more patient images comprise at least one of two-dimensional images and three-dimensional images of one or more portions of the patient's teeth.

58. The method of claim 44, wherein the method further comprises:
   providing a representation of one or more teeth of the defined three-dimensional maloccluded tooth/arch model;
   providing a representation of the one or more teeth of the defined three-dimensional maloccluded tooth/arch model in desired final positions represented by the prescription data; and
   changing patient information or prescription data resulting in a modification to the representation of one or more teeth of the defined three-dimensional maloccluded tooth/arch model or the representation of the one or more teeth of the defined three-dimensional maloccluded tooth/arch model in desired final positions represented by the prescription data.

* * * * *

UNITED STATES PATENT AND TRADEMARK OFFICE
CERTIFICATE OF CORRECTION

PATENT NO. : 7,155,373 B2
APPLICATION NO. : 10/081220
DATED : December 26, 2006
INVENTOR(S) : Russell A. Jordan It is certified that error appears in the above-identified patent and that said Letters Patent is hereby corrected as shown below:

Sheet 6 of 16 (Fig. 6)
Line 2, Box 204, After "of the" delete "the".
Line 2, Box 206, After "wire" insert -- . --.
Line 4, Box 212, After "and lower" delete "lower".

Column 16
Line 30, Delete "$W_{n-1}=0.$" and insert -- $W_{n-1}=0,$ --, therefor.

Column 19
Line 37, Delete "fall" and insert -- full --, therefor.

Column 22
Line 36, Delete "If A" and insert -- If $\Delta$ --, therefor.

Column 30
Line 40, In Claim 28, delete "mare" and insert -- more --, therefor.
Line 62, In Claim 29, delete "toot" and insert -- tooh --, therefor.

Column 34
Line 61, In Claim 54, after "from" delete "the" and insert -- a --, therefor.

Signed and Sealed this

Third Day of April, 2007

JON W. DUDAS
*Director of the United States Patent and Trademark Office*